United States Patent
Pan et al.

(10) Patent No.: US 9,657,328 B2
(45) Date of Patent: May 23, 2017

(54) METHODS FOR MODULATING THERMOSTABILITY AND ACID TOLERANCE OF MICROBES

(75) Inventors: Jae-Gu Pan, Chungnam (KR); Mor Dukhova Elena Anatolievna, Daejeon (KR)

(73) Assignee: Korean Research Institute of Bioscience and Biotechnology, Yuseong-Gu (KR)

( * ) Notice: Subject to any disclaimer, the term of this patent is extended or adjusted under 35 U.S.C. 154(b) by 854 days.

(21) Appl. No.: 12/558,218

(22) Filed: Sep. 11, 2009

(65) Prior Publication Data

US 2010/0151505 A1 Jun. 17, 2010

(30) Foreign Application Priority Data

Dec. 12, 2008 (KR) ........................ 10-2008-0126505

(51) Int. Cl.
*C12Q 1/48* (2006.01)
*C12N 1/36* (2006.01)
*C12N 9/10* (2006.01)

(52) U.S. Cl.
CPC ................. *C12Q 1/48* (2013.01); *C12N 1/36* (2013.01); *C12N 9/1029* (2013.01)

(58) Field of Classification Search
None
See application file for complete search history.

(56) References Cited

U.S. PATENT DOCUMENTS

| 7,195,897 B2* | 3/2007 | Leonhartsberger et al. . 435/113 |
| 7,319,142 B1* | 1/2008 | Goldman et al. ............ 536/23.1 |
| 2002/0137094 A1 | 9/2002 | Yamagishi |
| 2005/0233308 A1 | 10/2005 | Nishio et al. |

OTHER PUBLICATIONS

Hwang et al., (J. of Bacteriology, vol. 184, No. 5, Mar. 2002, p. 1277-1286).*
Metabolic Engineering VII: Health and Sustainability; "Improved Thermostability and Acetic Acid Tolerance of *Escherichia coli* by Directed Evolution of Homoserine O-Succinyltransferase"; Kribb, Jae-Gu Pan; 2008; pp. 100.
PLOS Biology; "Oxidative Stress Inactivates Cobalamin-Independent Methionine Synthase (MetE) in *Escherichia coli*"; Hondorp, Elise R., et al.; 2004; vol. 2, Issue 11, pp. 1738-1753.
Microbiology; "Inhibition of *Escherichia coli* Growth by Acetic Acid: a Problem with Methionine Biosynthesis and Homocysteine Toxicity" Roe, Andrew J. et al.; 2002, pp. 2215-2222.
Journal of Bacteriology; "Growth Rate of *Escherichia coli* at Elevated Temperatures: Reversible Inhibition of Homoserine Trans-Succinylase" Ron, Eliora Z., et al.; 1971, pp. 397-400.

* cited by examiner

*Primary Examiner* — Hope Robinson
(74) *Attorney, Agent, or Firm* — Locke Lord LLP; Gabriel J. McCool

(57) ABSTRACT

The present invention relates to a method for modulating thermostability or acid tolerance of a microbe by mutating a nucleic acid molecule encoding a homoserine o-succinyltransferase (MetA) to obtain a nucleic acid molecule encoding a mutant MetA and transforming a microbial cell with the nucleic acid molecule encoding a mutant MetA. The microbe, a bacteria expressing the mutant MetA of the present invention represents a growth rate improved in a vigorous environment such as higher-temperatures and/or lower pH conditions.

9 Claims, 15 Drawing Sheets

Fig. 10B

```
Geobacillus     MPINIPKDLPAKEILEQENIPVMDEERAYSQDIRPLMIILNLMPEK--EKAETQLLRLL    58
Clostridium     MPIKIPDSLPANEVLTMENIFVMDEHRALHQDVRPLRIATINLMPTK--ITTETQLLRLI    58
Thermotoga      MPIMVPSGLPAVKVLAKEGIPVMTERRAIHQDIRPLEILILNLMPDK---IKTEIQLLRLL   58
Streptococcus   MPIKLDNKLPALDVLRSENVPIMDENRASSQDIRPMEVLILNLMPTK--EVTETQLLRLL    58
Escherichia     MPIRVPDELPAVNFLRBENVFVMTTSRASGQEIRPLKVLIELNLMPKK--IETENQFLRLL    58
Methylococcus   MPLVAHTDLPTPQRLREEQQDVLSVERAARQDIREMHIGLLNMMPDAALEATERQFFRLV    60
                 ***  : :*      :   :  *   :  **:  :**: : **** :    :*  *:*

Geobacillus     G--MSPLQVNVTPLRPATHEPKTTSKHHLEQFYTIFPHIRURKFPDSMITTGAPVEQMPFE  116
Clostridium     G--NTPLQVEIELLHPKTHVSKNTPEEBILTKFYKTPDEVKDEKFUGLLITGAPVEQMEFE  116
Thermotoga      G--NTPLQVNVTLLYTETHKPKHTPIEHILKFYTTFSAVKDRKFIGFIITGAPVELLPFE  116
Streptococcus   A--NTPLQIMVEFLYMASHKSKNTHAEHMETPYKTFPDEIKDKYFDGLIVTGAPVEQMPFE  116
Escherichia     S--NSPLQVDIQLLRIDSRESRNTPAEHLMNFYCNFEDIQDQNFPGLIVTGAPLGLVEFN  116
Methylococcus   GRANVQFHMHPPTIEGLPGDQAEHIARYYESFDRIREEGLDGLIVSGAMVTQPHLQ      120
                      *  : :           :         :     *       ::*:**    .  : 
                    [Ser61Thr]

Geobacillus     EVNYWCELTEIMEMTKTMVTSTLHTCWGAQAQGLYYHYGIPKYPLPBKCFQVFMATVEVKN  176
Clostridium     EVNYWEELKKIMDWSVHMVYSHMVYSTFHICWGAQPAALVHHYCIKKYPLKEKMPCIFPHRICKPN  176
Thermotoga      EVDYWEELTEIMEWSRHMVYSTMFICWAAQAGLYYFGIPKYELFQKLSGVYKRVAK-D     175
Streptococcus   EVDYWQELTRVFDWSKRHVYSTLHLCWGAQACGLYYKHGVDKFPLSEKLSCIYKQTVDMPE  176
Escherichia     DVAYWPOIKQVLPHSKDHVTSTLPVCWAVCQAALMILVGIPKQTRTEKLSGVYEHHILHPH  176
Methylococcus   QRAFWQPLTEVFDNARSMVTSILCSCLATHALFQLSYGVERTHLLGFKRWGVYSHRVVEPL  180
                      *                  :   :      ::*
```

Fig. 10B(continued)

```
Geobacillus    VKLLRGFDDVPRMPHSRHTDVKREDIEVPDLTLLSNDKAGVCLVASNDQ-PRIPLTQH 235
Clostridium    TMLLRGFDDCFYAPHSRHTEYRRED EVGEIDILLSERAGVYIMKITRQG-QDIFYTQH 235
Thermotoga     SVLFRGHDDFFWAPHSRTEVKKEDIDKVPELETLLSRAGVYVRRKSE-RDLFYTQH 234
Streptococcus  NFLMMGFDDSFVSPHSRYTAVTLEDIQNKTPLDVVTKQEVGLSILASKDL-RLLFYSFQH 235
Escherichia    ALLTRGFDDISPLAPHERYADFPAALIRDYTDLEILTERGDAYLFASKDK-DLIFYTQH 235
Methylococcus  HDLVADINTRPDVPHSPYNE I FREDMERAG-LRVSRAGVHLLAVSPDLTYPDAH 239
                *        *               .             . *

Geobacillus    PEYDATTLKEYERDLAKGLP-----THIPESYF------------------ 264
Clostridium    SEYDQFTLKEYERDLAKGLK-----IKMPQKYF------------------ 264
Thermotoga     PEYDRYTLRDBYTRDIGRNLK-----VPIPANYF------------------ 263
Streptococcus  PEYDRQTLARBYRRDLEVGIN-----PDVPANYF------------------ 264
Escherichia    PEYDAQTLAQEFPRDVEAGLD-----PDVPYNYF------------------ 264
Methylococcus  PEYDTVSLKEYZREILKYTSGEREDYPFPEHYFSLEVGAALMDYVGALRSARRAGRAP 299
                **.     *        .                  *  *

Geobacillus    ---EMQDPSQPLNTWRPSHANLLFVRWLNYYVQETPYEWE------------------- 302  SEQ ID NO:37
Clostridium    ---PEYDPTKPVVWRGHANLLFSRWLNYVYVQTPEILNELK------------------- 305  SEQ ID NO:38
Thermotoga     ---PNWDPTKTPLLTWKSHAHLFFSRHLMYCIYQKTPYRLEDIH------------------- 304  SEQ ID NO:39
Streptococcus  ---PGLPEPAQPTKLRWRILAASTFFSAWINYAVYQETPYRLEEDDFSFYQYL---- 314  SEQ ID NO:40
Escherichia    ---PEWDPQYPYRASWRSHGHLLFTWWLNYYYQITPYDLRHMKPTLD-------- 309  SEQ ID NO:41
Methylococcus  PPFPEWDPCHPVIHKDNTWRDTRKAVFNNNLSKYQITDQDRREKPPMAHIDPDMPLGLA 355  SEQ ID NO:42
                                *  *
```

METHODS FOR MODULATING THERMOSTABILITY AND ACID TOLERANCE OF MICROBES

CROSS-REFERENCE TO RELATED APPLICATION

This application claims under 35 U.S.C. §119(a) the benefit of Korean Application No. 10-2008-0126505 filed Dec. 12, 2008, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Jul. 5, 2012, is named 84821_30151_SequenceListing.txt and is 40,456 bytes in size.

TECHNICAL FIELD

The present invention relates to a method for modulating (i.e., enhancing or decreasing) the thermostability or acid tolerance of a microbe, and a homoserine o-succinyltransferase (MetA) mutant having an enhanced/decreased thermostability or acid tolerance.

BACKGROUND ART

Growth of *Escherichia coli*, a mesophilic bacterium, is limited at elevated temperatures (13, 14). Quite unexpectedly, earlier investigations showed that *E. coli* did not grow at temperatures above 44° C. because of the instability of a single protein, homoserine o-succinyltransferase (MetA) (13, 14, 15, 16). MetA (EC 2.1.3.46), the first enzyme in methionine biosynthesis (FIG. 1), catalyzes the transfer of succinate from succinyl-CoA to L-homoserine (3, 22). Recent findings report that $MetA_{E.coli}$ tends to unfold even at 25° C. in vitro; unfolding becomes maximal at 44° C. and is followed by massive aggregation (5). In vivo, the soluble fraction of cytoplasmic proteins lacks $MetA_{E.coli}$ at temperatures higher than 44° C. (5). MetA from *Salmonella enterica* is as sensitive to elevated temperature as to weak organic acids including benzoate, propionate and acetate (11). Moreover, hydrogen peroxide increases its sensitivity to both heat and acid and may oxidatively damage the destabilized MetA (11). Price-Carter and coworkers (11) suggested that an excess of $MetA_{S.enterica}$ synthesized at elevated temperatures and/or in the presence of weak organic acids leads to the accumulation of insoluble aggregates that are toxic to the cells and inhibit bacterial growth.

In view of all the foregoing data and the fact that MetA occupies the control point in methionine biosynthesis, it has been proposed that MetA plays a central role in the control of bacterial growth (2). MetA's high sensitivity to many stress factors suggests that it may serve as a sort of metabolic fuse, detecting unfavorable growth conditions (11). In this connection, it is notable that methionine relieves the inhibitory effect of high-temperature and acetic acid on *E. coli* growth (7, 12, 13, 14).

However, an attempt to enhance thermostability of *E. coli* by modifying an enzyme (particularly, MetA) responsible for the synthesis of methionine has not been reported yet. The reason is as follows: (a) it is problematic to enhance thermostability of the enzyme per se by modifying the enzyme of mesophilic bacteria; and (b) it is quite difficult to expect whether its modification enhances the growth rate of bacteria at a high-temperature.

For example, US Pat. Appln. Pub. No. 20050233308 discloses a method for enhancing thermostability of an enzyme by substituting Arg, Thr and Ala residues for Lys, Ser and Ser residues of the protein, respectively. However, this specification predicts only amino acid residues implicated in thermostability of enzymes through orthologs study of mesophilic bacteria (*Corynebacterium glutamicum*) and thermophilic bacteria (*Corynebacterium efficiens*) with no practical experiments. In other words, this patent document provide no practical data on enhancing thermostability of enzymes per se via protein modification or evolution, and did not disclose that its modification or evolution permits to enhance the growth rate of bacteria at higher temperatures. Furthermore, this patent never discloses MetA which is a target enzyme of the present invention.

US Pat. Appln. Pub. No. 20020137094 discloses a method for predicting amino acid residues pivotal in protein thermostability via a multiple alignment of protein sequences. This patent document also provides no practical data on enhancing thermostability of enzymes per se via protein modification or evolution, and never discloses that its modification or evolution contributes to enhancing the growth rate of bacteria at higher temperatures.

In these connections, it would be a quite interesting to widen the optimum growth temperatures of *E. coli* by increasing the stability of the MetA enzyme, which is one of aims of the present invention.

The above information disclosed in this Background Art section is only for enhancement of understanding of the background of the invention and therefore it may contain information that does not form the prior art that is already known in this country to a person of ordinary skill in the art.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY OF THE DISCLOSURE

The present inventors have made intensive researches to develop novel methods for greatly enhancing/decreasing a growth of *E. coli* at mild/higher temperatures and/or under an acid condition. As results, we have discovered that the growth of bacteria at mild/high-temperatures and/or under an acid condition could be enhanced/decreased by substitution mutations of the wild-type homoserine o-succinyltransferase (MetA).

Accordingly, it is an object of this invention to provide a method for modulating thermostability or acid tolerance of a homoserine o-succinyltransferase (MetA).

It is another object of this invention to provide a method for modulating thermostability or acid tolerance of a microbe.

It is still another object of this invention to provide a homoserine o-succinyltransferase (MetA) having an modulating thermostability or acid tolerance.

It is still another object of this invention to provide a nucleic acid molecule encoding the mutant homoserine o-succinyltransferase (MetA).

It is further still another object of this invention to provide a recombinant vector comprising the mutant nucleic acid molecule.

It is further still another object of this invention to provide a host cell transformed with the mutant nucleic acid molecule.

Other objects and advantages of the present invention will become apparent from the following detailed description together with the appended claims and drawings.

DETAILED DESCRIPTION OF EMBODIMENTS

Figure 1:
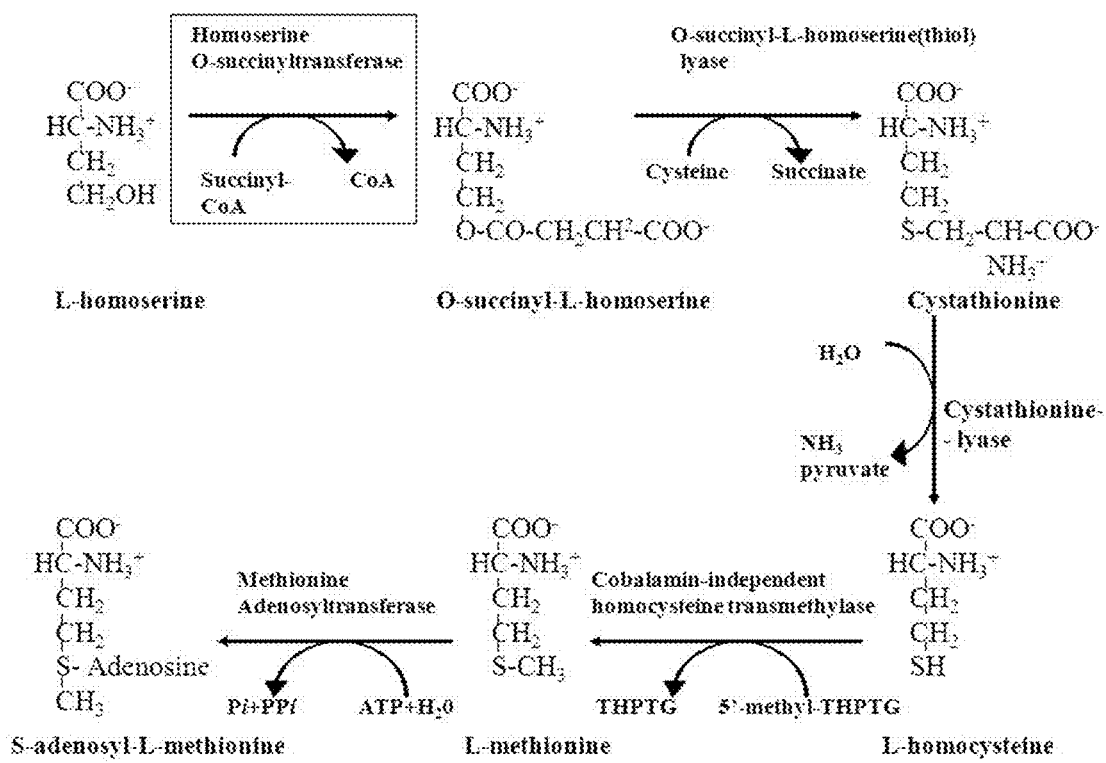
FIG. 1 schematically represents biosynthesis of L-methionine and S-adenosyl-L-methionine in *E. coli*. Abbreviations: 5'-methyl-THPTG—5'-methyltetrahydropteroyl-tri-L-glutamate; THPTG—tetrahydropteroyl-tri-L-glutamate.

In one aspect of this invention, there is provided a method for modulating (enhancing/decreasing) thermostability or acid tolerance of a microbe, comprising the steps of: (a) conferring a substitution mutation to a homoserine o-succinyltransferase (MetA)-encoding nucleotide sequence; and (b) transforming the MetA-encoding nucleotide sequence into a cell of the microbe.

In another aspect of this invention, there is provided a method for modulating thermostability or acid tolerance of a cell, comprising transforming the cell with a homoserine o-succinyltransferase (MetA)-encoding nucleotide sequence comprising the substitution of: (a) Thr for Ser at position 61; (b) Val for Glu at position 213; (c) Thr for Ile at position 229; (d) Asp for Asn at position 267; (e) Lys for Asn at position 271; (f) Lys for Gln at position 96; (g) Val for Leu at position 110; (h) Leu for Ile at position 124; (i) Leu for Arg at position 160; U) Thr for Ala at position 195; (k) Glu for Ala at position 200; (l) Gly for Asp at position 218; (m) Tyr for Ile at position 229; (n) Tyr for Phe at position 247; or (o) a combination thereof.

The present inventors have made intensive researches to develop novel methods for greatly enhancing/decreasing a growth of a microbe, preferably bacteria and more preferably E. coli at mild/higher temperatures and/or under an acid condition. As results, we have discovered that the growth of bacteria at mild/high-temperatures and/or under an acid condition could be improved/decreased by substitution mutations of the wild-type homoserine o-succinyltransferase (MetA).

The method of the present invention permits to enhance/ decrease thermostabiltiy or acid tolerance of MetA through MetA mutation, and mutated MetA gene is transformed into cells, improving/decreasing a cell growth at mild/higher and/or under acid conditions.

The present invention is a first invention to improve/ decrease thermostability and/or add tolerance of a microbe by modifying MetA.

The method of this invention may be expressed as "a method for enhancing/decreasing thermostability and/or acid tolerance of a microbe", or "a method for improving/ decreasing a growth rate of a microbe at a mild/high-temperature and/or under an acid condition".

According to the method of this invention, a substitution for enhancing/decreasing thermostability and/or acid tolerance of a microbe may be carried out in several positions of MetA.

Preferably, the substitution of MetA includes the substitution of: (a) Thr for Ser at position 61; (b) Val for Glu at position 213; (c) Thr for Ile at position 229; (d) Asp for Asn at position 267; (e) Lys for Asn at position 271; (f) Lys for Gln at position 96; (g) Val for Leu at position 110; (h) Leu for Ile at position 124; (i) Leu for Arg at position 160; (j) Thr for Ala at position 195; (k) Glu for Ala at position 200; (l) Gly for Asp at position 218; (m) Tyr for Ile at position 229; (n) Tyr for Phe at position 247; or (o) a combination thereof.

According to a more preferable embodiment, the substitution mutation induces the enhancement of the thermostability or acid tolerance of the microbe and comprises the substitution of: (a) Thr for Ser at position 61; (b) Val for Glu at position 213; (c) Thr for Ile at position 229; (d) Asp for Asn at position 267; (e) Lys for Asn at position 271; (f) Lys for Gln at position 96; (g) Val for Leu at position 110; (h) Leu for Ile at position 124; (k) Glu for Ala at position 200; (m) Tyr for Ile at position 229; (n) Tyr for Phe at position 247; or (o) a combination thereof.

According to a more preferable embodiment, the substitution mutation induces the decrease of the thermostability or acid tolerance of the microbe and comprises the substitution of: (i) Leu for Arg at position 160; (j) Thr for Ala at position 195; (l) Gly for Asp at position 218; or (o) a combination thereof.

The position of an amino acid residue referred as an amino acid sequence of MetA in this specification is described according to the amino acid sequence of MetA$_{E.\ coli}$ (SEQ ID NO:2).

According to a preferable embodiment, the substitution of (a) Thr for Ser at 61 position is the substitution of Thr for Ser at position 4 in the Leu-Ser-Asn-Ser-Pro-Leu-Gln-Val amino acid sequence (SEQ ID NO:46) of MetA; the substitution of (b) Val for Glu at position 213 is the substitution of Val for Glu at position 4 in the Ile-Leu-Ala-Glu-Thr-Glu-Xaa$_1$-Gly (Xaa$_1$ represents Asp (SEQ ID NO:47) or Glu (SEQ ID NO:48)) amino acid sequence of MetA; the substitution of (c) Thr for Ile at position 229 is the substitution of Thr for Ile at position 4 in the Asp-Lys-Arg-Ile-Ala-Phe-Val-Thr amino acid sequence (SEQ ID NO:49) of MetA; the substitution of (d) Asp for Asn at position 267 is the substitution of Asp for Asn in the Tyr-Phe-Pro-Xaa$_1$-Asn-Asp-Pro-Gln (Xaa$_1$ represents Lys (SEQ ID NO:50), His (SEQ ID NO:51) or Gln (SEQ ID NO:52)) amino acid sequence of MetA; the substitution of (e) Lys for Asn at position 271 is the substitution of Lys for Asn at position 4 in the Asp-Pro-Gln-Asn-Xaa$_1$-Pro-Arg-Ala (Xaa$_1$ represents Lys (SEQ ID NO:53), Ile (SEQ ID NO:54) or Thr (SEQ ID NO:55)); the substitution of (f) Lys for Gln at 96 position is the substitution of Lys for Gln at position 4 in the Xaa$_1$-Xaa$_2$-Ile-Gln-Asp-Gln-Asn-Phe (Xaa$_1$ and Xaa$_2$ independently represent Glu or Asp) amino acid sequence (SEQ ID NO:56) of MetA; the substitution of (g) Val for Leu at 110 position is the substitution of Val for Leu at position 4 in the Gly-Ala-Pro-Leu-Gly-Leu-Val-Glu amino acid sequence (SEQ ID NO:57) of MetA; the substitution of (h) Leu for Ile at 124 position is the substitution of Leu for Ile at position 4 in the Trp-Pro-Gln-Ile-Xaa$_1$-Gln-Val-Leu (Xaa$_1$ represents Lys (SEQ ID NO:58) or Arg (SEQ ID NO:59)) amino acid sequence of MetA; the substitution of (i) Leu for Arg at 160 position is the substitution of Leu for Arg at position 4 in the Lys-Gln-Thr-Arg-Xaa$_1$-Xaa$_2$-Lys-Xaa$_3$ (Xaa$_1$ represents Ile, Thr or Ala; Xaa$_2$ represents Asp or Glu; Xaa$_3$ represents Leu or Ile) amino acid sequence (SEQ ID NO:60) of MetA; the substitution of (j) Thr for Ala at 195 position is the substitution of Thr for Ala at position 4 in the Ser-Arg-Tyr-Ala-Asp-Phe-Pro-Xaa$_1$ (Xaa$_1$ represents Arg (SEQ ID NO:61) or Gly (SEQ ID NO:62)) amino acid sequence of MetA; the substitution of (k) Glu for Ala at 200 position is the substitution of Glu for Ala at position 4 in the Phe-Pro-Ala-Ala-Leu-Ile-Arg-Asp amino acid sequence (SEQ ID NO:63) of MetA; the substitution of (l) Gly for Asp at 218 position is the substitution of Gly for Asp at position 4 in the Glu-Xaa$_1$-Gly-Asp-Ala-Tyr-Leu-Phe (Xaa$_1$ represents Asp (SEQ ID NO:64) or Glu (SEQ ID NO:65)) amino acid sequence of MetA; the substitution of (m) Tyr for Ile at 229 position is the substitution of Tyr for Ile at position 4 in the Asp-Lys-Arg-Ile-Ala-Phe-Val-Thr amino acid sequence (SEQ ID NO:66) of MetA; the substitution of (n) Tyr for Phe at 247 position is the substitution of Tyr for Phe at position 4 in the Ala-Xaa$_1$-Glu-Phe-Phe-Arg-Asp-Val (Xaa$_1$ represents Ser (SEQ ID NO:67), Gln (SEQ ID NO:68) or Gly (SEQ ID NO:69)) amino acid sequence of MetA; or (o) a combination thereof.

According to a more preferable embodiment, the substitution comprises the substitution of: (c) Thr for Ile at position 229; (d) Asp for Asn at position 267; (e) Lys for Gln at position 96; (h) Leu for Ile at position 124; (i) Leu for Arg at position 160; (m) Tyr for Ile at position 229; or (o) a combination thereof.

A substitution mutation of a particular amino acid in MetA may be carried out according to various methods known to those ordinarily skilled in the art. For example, the substitution mutation may be performed by a method including a PCR mutagenesis, a transposon mutagenesis, a site-directed mutagenesis, an insertional mutagenesis and a cassette mutagenesis, and preferably a site-directed mutagenesis which may be carried out using PCR (Sambrook et al., Molecular Cloning, A Laboratory Manual, Cold Spring Harbor Laboratory Press (2001)). The site-directed mutagenesis using PCR utilizes the primer having a sequence in which a base at a specific site is substituted.

The procedure to transform a mutated MetA-encoding sequence into a cell may be carried out according to various methods known to those ordinarily skilled in the art. For example, the transformation may be performed using a CaCl$_2$ method (Cohen, S. N. et al., Proc. Natl. Acac. Sci. USA, 9: 2110-2114 (1973)), a Hanahan method (Cohen, S.

N. et al., *Proc. Natl. Acac. Sci. USA*, 9: 2110-2114 (1973); and Hanahan, D., *J. Mol. Biol.*, 166: 557-580 (1983)) and an electroporation method (Dower, W. J. et al., *Nucleic. Acids Res.*, 16: 6127-6145 (1988)).

According to a preferable embodiment, the MetA of the present invention is derived from a mesophilic bacterium. The term "mesophilic bacterium" used in the present invention refers to a bacterium having the most high growth rate at a mild temperature, typically 15-40° C. Preferably, the mesophilic bacterium includes *Escherichia, Pseudomonas, Xanthomonas, Serratia, Lactobacillus, Bacillus, Citrobacter, Salmonella* or *Klebsiella*, more preferably *Escherichia coli, Pseudomonas aeruginosa, Xanthomonas rinicola, Serratia marcescens, Lactobacillus lactis, Bacillus subtilis, Citrobacter freundii, Salmonella enterica* or *Klebsiella pneumonia*, and most preferably *Escherichia coli*.

According to a preferable embodiment, the cell transformed with MetA-encoding nucleotide sequence is the mesophilic bacterium, more preferably *Escherichia, Pseudomonas, Xanthomonas, Serratia, Lactobacillus, Bacillus, Citrobacter; Salmonella* or *Klebsiella*, much more preferably *Escherichia coli, Pseudomonas aeruginosa, Xanthomonas rinicola, Serratia marcescens, Lactobacillus lactis, Bacillus subtilis, Citrobacter freundii, Salmonella enterica* or *Klebsiella pneumoniae*, and most preferably *Escherichia coli*.

According to the method of the present invention, thermostability and/or acid tolerance of MetA is remarkably increased/decreased, resulting in enhancing/decreasing thermostability and/or acid tolerance of a transformed cell containing MetA.

The term "thermostabiltiy" used herein in conjunction with microbes means that microbes have a potential to grow at higher temperatures (generally 20-60° C., preferably 30-50° C., more preferably 30-48° C. and most preferably 30-44° C.). The term "thermostabiltiy" used herein in conjunction with MetA is intended to mean the stability of the enzyme to thermal influence. All enzyme proteins are destabilized and eventually degraded with increasing temperature, each enzyme protein having a certain temperature range wherein the protein is stable and retains its enzymatic activity. Increased thermostability means that the enzyme protein may retain its enzymatic activity and/or exhibit a higher relative activity at increased temperatures.

The term "acid tolerance" used herein in conjunction with microbes means that microbes have a potential to grow under acid conditions (i.e., at low pH conditions). The term "acid tolerance" used herein in conjunction with MetA is intended to mean the stability of the enzyme to lower pH influence.

The present invention enables bioprocesses to be effectively carried out using microbes at high-temperatures and/or under acid conditions.

Figure 10A:
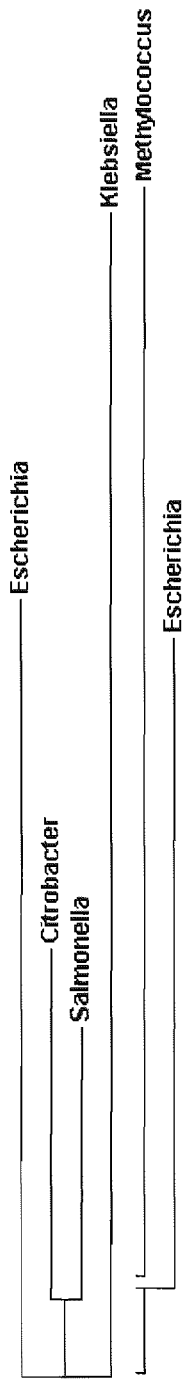
FIG. 10 shows a phylogeny tree (A) and multiple alignment (B) of MetA amino acid sequences from *E. coli* and thermophilic bacteria. Abbreviations: Geobacillus—*Geobacillus kaustophilus* HTA426 (YP_147640.1), Clostridium—*Clostridium thermocellum* ATCC 27405 (YP_001038259.1), Thermotoga—*Thermotoga maritima* ATCC 43589 (NP_228689.1), Streptococcus—*Streptococcus thermophilus* ATCC 51836 (YP_141582.1), Methylococcus—*Methylococcus capsulatus* str. Bath (YP_114313.1). Symbols: *, matched amino acids; *, similar amino acids; $\overset{*}{*}$, very similar amino acids.
Figure 11A:
FIG. 11 shows a phylogeny tree (A) and multiple alignment (B) of MetA amino acid sequences from *E. coli* and mesophilic bacteria. Abbreviations: Citrobacter—*Citrobacter koseri* ATCC BAA-895 (YP_001455419.1), Salmonella—*Salmonella enterica* subsp. *enterica* serovar Paratyphi A str. ATCC 9150 (YP_153079.1), Escherichia—*Escherichia coli* (CAG29901), Klebsiella—*Klebsiella pneumoniae* subsp. *pneumoniae* MGH 78578 (YP_001338016.1). Symbols: *, matched amino acids; *, similar amino acids; $\overset{*}{*}$, very similar amino acids.
Figure 11B:
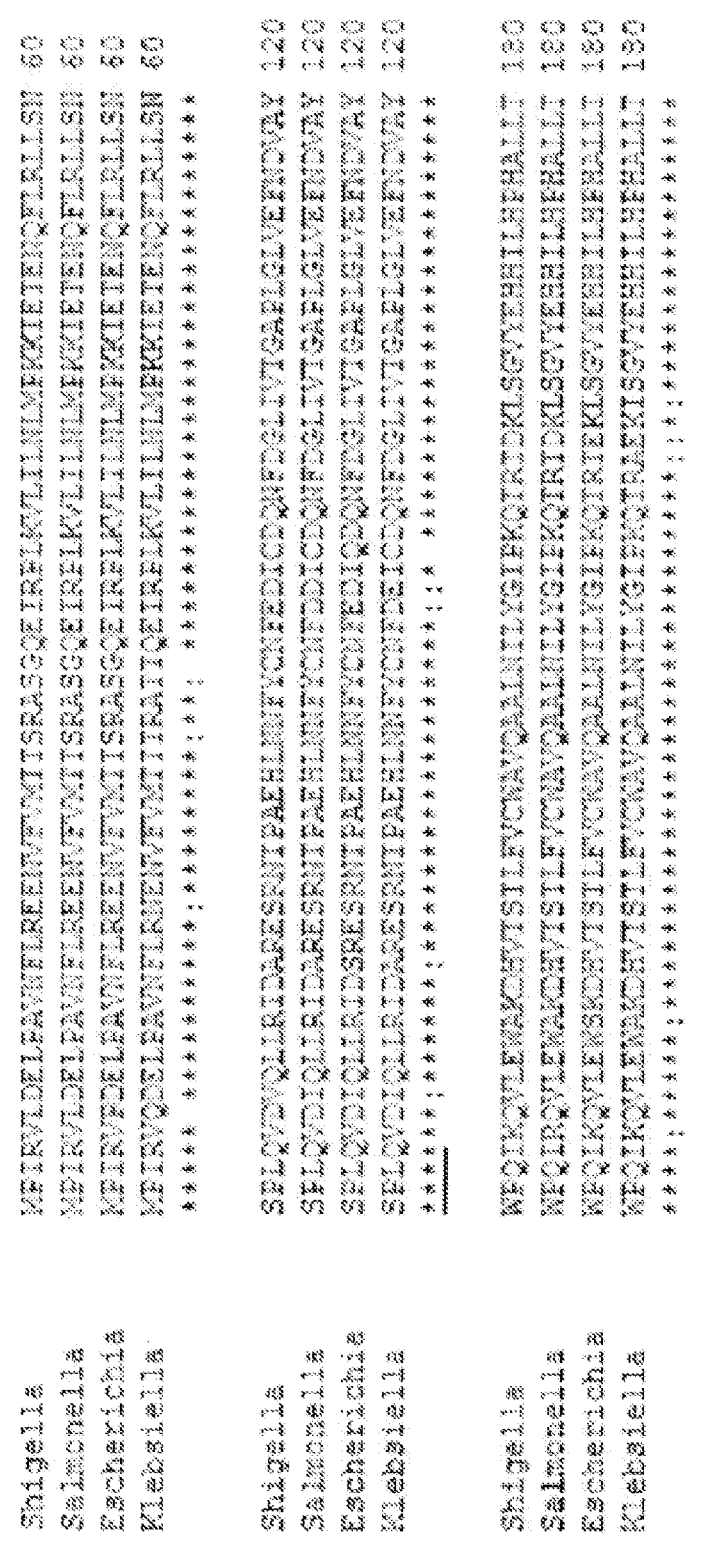
Figure 11B:
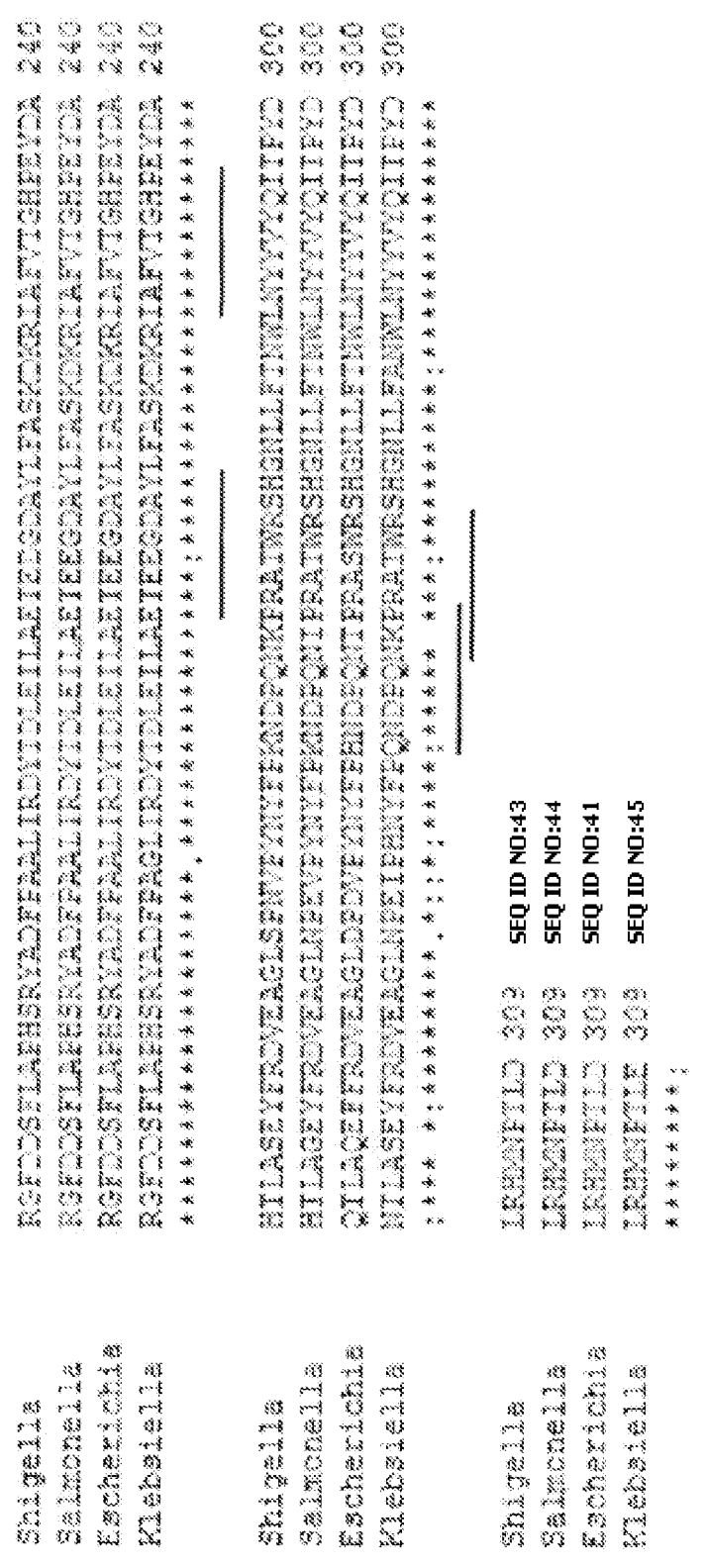

As indicated in FIGS. 10 and 11, MetA is found to be responsible for thermostability in a variety of bacteria and to have conserved sequences. In this regard, the mutagenesis approaches of the present invention for modulating thermostability or acid tolerance of bacterial cells or MetA may be applied to a large number of microbes including, preferably, *Escherichia, Pseudomonas, Xanthomonas, Serratia, Lactobacillus, Bacillus, Citrobacter, Salmonella* or *Klebsiella*, more preferably *Escherichia coli, Pseudomonas aeruginosa, Xanthomonas rinicola, Serratia marcescens, Lactobacillus lactis, Bacillus subtilis, Citrobacter freundii, Salmonella enterica* or *Klebsiella pneumonia*, and most preferably *Escherichia cob*:

In still another aspect of this invention, there is provided a homoserine o-succinyltransferase (MetA) having an enhanced/decreased thermostability or acid tolerance, comprising conferring a substitution mutation to MetA having the substitution of: (a) Thr for Ser at position 61; (b) Val for Glu at position 213; (c) Thr for Ile at position 229; (d) Asp for Asn at position 267; (e) Lys for Asn at position 271; (f) Lys for Gln at position 96; (g) Val for Leu at position 110; (h) Leu for Ile at position 124; (i) Leu for Arg at position 160; (j) Thr for Ala at position 195; (k) Glu for Ala at position 200; (l) Gly for Asp at position 218; (m) Tyr for Ile at position 229; (n) Tyr for Phe at position 247; or (o) a combination thereof.

According to a preferable embodiment, the substitution of (a) Thr for Ser at 61 position is the substitution of Thr for Ser at position 4 in the Leu-Ser-Asn-Ser-Pro-Leu-Gln-Val amino acid sequence (SEQ ID NO:46) of MetA; the substitution of (b) Val for Glu at position 213 is the substitution of Val for Glu at position 4 in the Ile-Leu-Ala-Glu-Thr-Glu-$Xaa_1$-Gly ($Xaa_1$ represents Asp (SEQ ID NO:47) or Glu (SEQ ID NO:48)) amino acid sequence of MetA; the substitution of (c) Thr for Ile at position 229 is the substitution of Thr for Ile at position 4 in the Asp-Lys-Arg-Ile-Ala-Phe-Val-Thr amino acid sequence (SEQ ID NO:49) of MetA; the substitution of (d) Asp for Asn at position 267 is the substitution of Asp for Asn in the Tyr-Phe-Pro-$Xaa_2$-Asn-Asp-Pro-Gln ($Xaa_2$ represents Lys (SEQ ID NO:50), His (SEQ ID NO:51) or Gln (SEQ ID NO:52)) amino acid sequence of MetA; the substitution of (e) Lys for Asn at position 271 is the substitution of Lys for Asn at position 4 in the Asp-Pro-Gln-Asn-$Xaa_3$-Pro-Arg-Ala ($Xaa_3$ represents Lys (SEQ ID NO:53), Ile (SEQ ID NO:54) or Thr (SEQ ID NO:55)); the substitution of (f) Lys for Gln at 96 position is the substitution of Lys for Gln at position 4 in the $Xaa_1$-$Xaa_2$-Ile-Gln-Asp-Gln-Asn-Phe ($Xaa_1$ and $Xaa_2$ independently represent Glu or Asp) amino acid sequence (SEQ ID NO:56) of MetA; the substitution of (g) Val for Leu at 110 position is the substitution of Val for Leu at position 4 in the Gly-Ala-Pro-Leu-Gly-Leu-Val-Glu amino acid sequence (SEQ ID NO:57) of MetA; the substitution of (h) Leu for Ile at 124 position is the substitution of Leu for Ile at position 4 in the Trp-Pro-Gln-Ile-$Xaa_1$-Gln-Val-Leu ($Xaa_1$ represents Lys (SEQ ID NO:58) or Arg (SEQ ID NO:59)) amino acid sequence of MetA; the substitution of (i) Leu for Arg at 160 position is the substitution of Leu for Arg at position 4 in the Lys-Gln-Thr-Arg-$Xaa_1$-$Xaa_2$-Lys-$Xaa_3$ ($Xaa_1$ represents Ile, Thr or Ala; $Xaa_2$ represents Asp or Glu; $Xaa_3$ represents Leu or Ile) amino acid sequence (SEQ ID NO:60) of MetA; the substitution of (j) Thr for Ala at 195 position is the substitution of Thr for Ala at position 4 in the Ser-Arg-Tyr-Ala-Asp-Phe-Pro-$Xaa_1$ ($Xaa_1$ represents Arg (SEQ ID NO:61) or Gly (SEQ ID NO:62)) amino acid sequence of MetA; the substitution of (k) Glu for Ala at 200 position is the substitution of Glu for Ala at position 4 in the Phe-Pro-Ala-Ala-Leu-Ile-Arg-Asp amino acid sequence (SEQ ID NO:63) of MetA; the substitution of (l) Gly for Asp at 218 position is the substitution of Gly for Asp at position 4 in the Glu-$Xaa_1$-Gly-Asp-Ala-Tyr-Leu-Phe ($Xaa_1$ represents Asp (SEQ ID NO:64) or Glu (SEQ ID NO:65)) amino acid sequence of MetA; the substitution of (m) Tyr for Ile at 229 position is the substitution of Tyr for Ile at position 4 in the Asp-Lys-Arg-Ile-Ala-Phe-Val-Thr amino acid sequence (SEQ ID NO:66) of MetA; the substitution of (n) Tyr for Phe at 247 position is the substitution of Tyr for Phe at position 4 in the Ala-$Xaa_1$-Glu-Phe-Phe-Arg-Asp-Val ($Xaa_1$ represents Ser (SEQ ID NO:67), Gln (SEQ ID NO:68) or Gly (SEQ ID NO:69)) amino acid sequence of MetA; or (o) a combination thereof.

According to a more preferable embodiment, the substitution comprises the substitution of: (c) Thr for Ile at position 229; (d) Asp for Asn at position 267; (e) Lys for Gln at position 96; (h) Leu for Ile at position 124; (i) Leu for Arg at position 160; (m) Tyr for Ile at position 229; or (o) a combination thereof.

An illustrative example of the amino add sequence of mutated MetA protein in the present invention is described in SEQ ID NO:2.

In still another aspect of this invention, there is provided a nucleic acid molecule encoding the mutated homoserine o-succinyltransferase (MetA).

The term "nucleic acid molecule" as used herein refers to a comprehensive DNA (gDNA and cDNA) and RNA molecule, and a nucleotide as a basic unit in the nucleic acid includes not only natural nucleotides but also analogues which a sugar or base are modified (Scheit, *Nucleotide Analogs*, John Wiley, New York (1980); Uhlman and Peyman, *Chemical Reviews*, 90:543-584 (1990)).

An illustrative example of the mutated nucleic acid molecule in the present invention includes the nucleotide sequence as set forth in SEQ ID NO:1.

In further still another aspect of this invention, there is provided a recombinant vector containing the nucleic acid molecule encoding the mutated homoserine o-succinyltransferase (MetA).

The vector system of this invention may be constructed by various methods known to those skilled in the art which are disclosed in Sambrook et al., Molecular Cloning, A Laboratory Manual, Cold Spring Harbor Laboratory Press (2001), which is herein incorporated by reference.

Typically, the vector of this invention may be constructed as cloning or expression vector. The vector of the present invention may be constructed to utilize a prokaryotic or eukaryotic cell as a host. It is preferable to utilize a prokaryotic cell as a host in the senses that the nucleic acid molecule of the present invention is derived from the prokaryotic cell and the culture is convenient. The vector of this invention may be typically constructed as cloning or expression vector.

For example, the present vector which is expression vector and utilizes a prokaryotic cell as a host commonly includes a strong promoter (e.g., tac promoter, lac promoter, lacUV5 promoter, lpp promoter, $p_L^\lambda$ promoter, $p_R^\lambda$ promoter, rac5 promoter, amp promoter, recA promoter, SP6 promoter, trp promoter and T7 promoter, etc.) for transcription, a ribosome-binding site for translation, and transcription/translation termination sequence. The promoter and operator region of *E. coli* tryptophan biosynthesis pathway (Yanofsky, C., *J. Bacteriol.*, 158:1018-1024 (1984)), and $p_L^\lambda$ promoter (Herskowitz, I. and Hagen, D., *Ann. Rev. Genet.*, 14:399-445 (1980)) may be used as a regulatory region in *E. coli* utilized as a host.

Meanwhile, the vector capable of being used in the present invention may be prepared by manipulating a plasmid (example: pSC101, ColE1, pBR322, pUC8/9, pHC79, pUC19, pET, etc.), a phage (example: λgt4·λB, λ-Charon, λΔz1, M13, etc.) or a virus (example: SV40, etc.) known to those ordinarily skilled in the art.

The vector of this invention may be fused with other sequence to purify MetA expressed from the vector in a feasible manner. For example, a fusion sequence includes glutathione-S-transferase (Pharmacia, USA), maltose-binding protein (NEB, USA), FLAG (IBI, USA) and 6× His (hexahistidine; Quiagen, USA), and most preferably 6× His. Because of the additive sequences for purification, the protein expressed in the host may be purified by a chromatography in a high-throughput and easy manner.

According to a preferable embodiment, the fusion protein expressed by the vector containing the fusion sequence is purified by an affinity chromatography. For example, in a glutathione-S-transferase-fused protein, the glutathione may be used as a substrate for purification, and in a 6× His-fused protein, a Ni-NTA His-binding resin (Novagen, USA) may be used for purification. Consequently, desirable MetAs may be obtained in a high-throughput and easy manner.

On the other hand, the expression vector of this invention includes an antibiotics-resistance gene known to those ordinarily skilled in the art as a selection marker, for example resistant genes against ampicillin, gentamycin, carbenicillin, chloramphenicol, streptomycin, kanamycin, geneticin, neomycin and tetracycline.

In another aspect of this invention, there is provided a host cell transformed with the mutated nucleic acid molecule.

The host cell capable of cloning and expressing the vector of the present invention in a stable and successive manner may utilize any one of host cells known to those ordinarily skilled in the art, for example including *E. coli* JM109, *E. coli* BL21(DE3), *E. coli* RR1, *E. coli* LE392, *E. coli* B, *E. coli* X 1776, *E. coli* W3110, the genus *Bacillus* strains such as *Bacillus subtilis, Bacillus thuringiensis*, and *Enterococcus* and strains such as *Salmonella typhimurium, Serratia marcescens* and various *Pseudomonas* species.

The procedure to deliver the present vector into a cell may be carried out according to various methods known to those ordinarily skilled in the art. For example, the transformation using a prokaryotic cell as a host may be performed according to a $CaCl_2$ method (Cohen, S. N. et al., *Proc. Natl. Acac. Sci. USA*, 9: 2110-2114 (1973)), a Hanahan method (Cohen, S. N. et al., *Proc. Natl. Acac. Sci. USA*, 9:2110-2114 (1973); and Hanahan, D., *J. Mol. Biol.*, 166: 557-580 (1983)) and an electroporation method (Dower, W. J. et al., *Nucleic. Acids Res.*, 16: 6127-6145 (1988)).

The vector transferred to host cells may be expressed within the host cells, obtaining massive MetA. For example, gene expression in the expression vector containing lac promoter may be induced by treating IPTG in host cells.

As described above in detail, the present invention is a first report improving a growth rate of a microbe (e.g., *E. coli*) at high-temperatures only by stabilizing MetA. The stabilization of MetA enables to provide a new theoretical fundament to design a microbe platform, preferably a bacteria strain (e.g., *E. coli*) growing at higher-temperatures, and to carry out a bioprocess in an economical cost and time.

The features and advantages of this invention are summarized as follows:

(a) The present invention is a first report to modulate (i.e., enhance/decrease) thermostability and/or acid stability of a microbe by mutation of MetA.

(b) The mutated MetA of the present invention shows stability notably enhanced at high-temperatures and/or under acid conditions or decreased at mild temperature.

(c) The microbe, particular bacteria expressing the mutated MetA of the present invention represents a growth rate improved in a vigorous environment such as higher-temperatures and/or lower acid conditions.

The present invention will now be described in further detail by examples. It would be obvious to those skilled in the art that these examples are intended to be more concretely illustrative and the scope of the present invention as set forth in the appended claims is not limited to or by the examples.

EXAMPLES

Experimental Materials and Methods

Bacterial strains and plasmids. The strains and plasmids used in this study are listed in Table 1.

TABLE 1

Bacterial strains and plasmids

| Strain or Plasmid | Relevant description[a] | Source or reference |
|---|---|---|
| *E. Coli* | | |
| W3110 | Wild-type | Laboratory stock |
| DH5α | F-, supE44 hsdR17 recA1 gyrA96 endA1 thi-1 relA1 deoR λ- | (17) |
| JW3973 | F-, Δ(araD-araB)567, ΔlacZ4787(::rrnB-3), LAM-, rph-1, ΔmetA780::kan, Δ(rhaD-rhaB)568, Δ(rhaD-rhaB)568, hsdR514 | Keio collection (JP) |
| WE | JW3973 carrying non-mutated metA$_{E.coli}$ on the chromosome, prototroph | This study |
| 333 | JW3973 carrying mutated metA$_{E.coli}$-333 on the chromosome, prototroph | This study |
| T61 | JW3973 carrying metA$_{E.coli}$ with S61T substitution on the chromosome, prototroph | This study |
| V213 | JW3973 carrying metA$_{E.coli}$ with E213V substitution on the chromosome, prototroph | This study |
| T229 | JW3973 carrying metA$_{E.coli}$ with I229T substitution on the chromosome, prototroph | This study |
| D267 | JW3973 carrying metA$_{E.coli}$ with N267D substitution on the chromosome, prototroph | This study |
| K271 | JW3973 carrying metA$_{E.coli}$ with N271K substitution on the chromosome, prototroph | This study |
| WG | JW3973 carrying metA$_{Geo}$ on the chromosome, prototroph | This study |
| K96 | JW3973 carrying metA$_{E.coli}$ with Q96K substitution on the chromosome, prototroph | This study |
| V110 | JW3973 carrying metA$_{E.coli}$ with L110V substitution on the chromosome, prototroph | This study |
| L124 | JW3973 carrying metA$_{E.coli}$ with I124L substitution on the chromosome, prototroph | This study |
| L160 | JW3973 carrying metA$_{E.coli}$ with R160L substitution on the chromosome, prototroph | This study |
| T195 | JW3973 carrying metA$_{E.coli}$ with A195T substitution on the chromosome, prototroph | This study |
| E200 | JW3973 carrying metA$_{E.coli}$ with A200E substitution on the chromosome, prototroph | This study |
| G218 | JW3973 carrying metA$_{E.coli}$ with D218G substitution on the chromosome, prototroph | This study |
| Y229 | JW3973 carrying metA$_{E.coli}$ with I229Y substitution on the chromosome, prototroph | This study |
| Y247 | JW3973 carrying metA$_{E.coli}$ with F247Y substitution on the chromosome, prototroph | This study |
| BL21(DE3) | F-ompT hsdS$_B$(r-$_B$m-$_B$) gal dcm(DE3) | Novagen, USA |
| *Geobacillus kaustophilus* | Wild-type | KCTC 3397 |
| Plasmids | | |
| pACYC177 | Plasmid vector, Amp$^r$ Kan$^r$ | New England Biolabs, USA |
| pET22b | Expression vector, Amp$^r$ | Novagen, USA |
| pKD46 | λ Red (gam bet exo) ara C rep101(Ts) Amp$^r$ | (4) |
| pPmetA | pACYC17 carrying metAp$_{E.coli}$, Amp$^r$ | This study |
| pMetA | pPmetA carrying metA$_{E.coli}$, Amp$^r$ | This study |
| pMetA-333 | pPmetA carrying thermostable metA$_{E.coli}$, Amp$^r$ | This study |
| pGeo-MetA | pPmetA carrying metA$_{Geo}$, Amp$^r$ | This study |

[a]Amp$^r$, ampicillin resistance; Kan$^r$, kanamycin resistance; metAp$_{E.coli}$, promoter of *E. coli* metA gene; metA$_{E.coli}$, *E. coli* metA gene; metA$_{Geo}$, *G. kaustophilus* metA gene.

Growth Conditions.

The *E. coli* strains were grown in minimal M9 medium (17) supplemented with glucose (0.2%), LB (Difco, USA) or 2×YT (17). Antibiotics were used in the following concentrations: ampicillin—100 μg ml$^{-1}$, kanamycin—25 μg ml$^{-1}$. L-methionine was added to the medium to a final concentration of 50 μg ml$^{-1}$. The strain *Geobacillus kaustophilus* KCTC 3397 was cultivated aerobically in nutrient broth (Difco, USA) at 50° C.

Preparation of Plasmid DNA.

Plasmid DNA was Extracted from the Cells using a Plasmid mini prep kit (SolGent Co, Ltd., Korea). All the restriction enzymes used in this study were purchased from New England BioLabs Inc., USA.

Cloning of *E. coli* metA.

The natural promoter of metA was amplified from the genomic DNA of *E. coli* strain W3110 using the primers metA1 (CGCCTACTCGAGATCGCAACGAGTTCCTCC) (SEQ ID NO:3) and metA2 (GCCTCAAAGCTTCATATGCTGATTACCTCACTACATACGC) (SEQ ID NO:4), and was cloned into XhoI and HindIII sites of the plasmid vector pACYC177 to yield the plasmid pPmetA. The structural metA gene amplified from the genomic DNA of *E. coli* W3110 using the primers metA3 (CGCCTCCATATGCCGATTCGTGTGCCG) (SEQ ID NO:5) and metA4 (CGCCTCAAGCTTGGTGCCTGAGGTAAGGTGCTG) (SEQ ID NO:6) was cloned into NdeI and HindIII sites of the plasmid pPmetA to obtain the plasmid pMetA.

Cloning of metA from the Thermophilic Strain *G. Kaustophilus* KCTC 3397.

The metA$_{Geo}$ from the genomic DNA was amplified using the primers Geo1 (CGCCTCCATATGCCAATCAACATTCCAAAAG) (SEQ ID NO:10) and Geo2 (CAGGGCGATTGTCGAAACACG) (SEQ ID NO:11) and cloned into an NdeI restriction site of the plasmid pPmetA. The resulting plasmid pGeo-MetA was transferred into the strain *E. coli* JW3973 (ΔmetA). The transformed cells were incubated on minimal M9 plates supplemented with glucose and ampicillin.

Library Construction and Selection of Thermostable metA Mutants.

The metA together with its promoter region was isolated from the pMetA plasmid, gel-purified and used as a template for error-prone PCR. Random mutagenesis was performed with a Diversify PCR Random Mutagenesis Kit (Clontech Laboratories, Inc., USA) to obtain 3, 5 and 8 nucleotide substitutions per kb. The PCR conditions were as described in the manual using the primers metA5 (GTAGTGAGGTAATCAGCATATG) (SEQ ID NO:7) and metA4 (SEQ ID NO:6). The PCR products were purified using a QIAquick PCR Purification Kit (Qiagen, USA), amplified one more time using the same primers and TaKaRa Ex Taq polymerase, digested with the restriction enzymes NdeI and HindIII and cloned into the plasmid pPmetA. The resulting DNA mixture was transferred into freshly prepared *E. coli* JW3973(ΔmetA) cells by electroporation. The transformed cells were incubated at 37° C. on M9 plates supplemented with glucose and ampicillin. The clones were then cultivated on solid M9 glucose medium at 44° C. to select the growing ones. The fastest-growing mutant was identified during the cultivation in liquid M9 glucose medium at 44° C.

Incorporation of metA Mutants into the *E. coli* Chromosome.

The metA mutants were transferred into the *E. coli* JW3973 (ΔmetA) chromosome using the lambda Red recombination system (4). The structural genes flanked by 50 bp nucleotide sequences up- and down-stream were synthesized using the primers metA8 (ATCTGGATGTCTAAACGTATAAGCGTATGTAGTGAGG) (SEQ ID NO:8) and metA9 (ATCGCTTAACGATCGACTATCACAGAAGATTAATCC) (SEQ ID NO:9), Vent polymerase (New England BioLabs Inc., USA) and the corresponding plasmids as templates. *G. kaustophilus* metA was amplified from the genomic DNA as template using the primers Geo4 (ATCTGGATGTCTAAACGTATAAGCGTATGTAGTGAGGTAATCAGGTTATGCCAATCAACATTCC) (SEQ ID NO:12) and Geo5 (ATCGCTTAACGATCGACTATCACAGAAG ATTAATCCAGCGTTGGATTCATCAGGGCGATTGTCGAAACACG) (SEQ ID NO:13). Freshly-prepared competent cells of the strain *E. coli* JW3973 (ΔmetA) harboring the helper plasmid pKD46 were transformed with 150 μg of PCR products by electroporation as described (4).

The transformed cells were incubated on M9 methionine deficient medium plates supplemented with glucose at 37° C. The grown colonies were checked for loss of kanamycin resistance and cultivated on nonselective LB plates at 43° C. to eliminate the plasmid pKD46. The inserted metA mutants were amplified from the chromosome and sequenced.

Site-Directed Mutagenesis of metA.

To introduce multiple direct mutations into metA a Quick Change Multi Site-Directed Mutagenesis kit (Stratagene, USA) was employed. The primers used were metT (GCCTGCTTTCAAACACACACCTTTGCAGGTCG) (SEQ ID NO:14), metD (CTATTTCCCGCACGATGATCCGCAAAATACACC) (SEQ ID NO:16), metK (GATCCGCAAAAGACACCGCGAGCGAGC) (SEQ ID NO:17), metT2 (GCCAGTAAA GATAAGCGCACTGCC TTTGTGACG) (SEQ ID NO:15) and metV (CTGGAAATTCTGGCAGTGACGGAAGAAGGG) (SEQ ID NO:18).

The other site-directed metA mutants were obtained using a KOD-Plus-Mutagenesis Kit (Toyobo Co., Ltd) according to the manufacturer's protocol. Plasmid pMetA was used as a template, and the primers are shown in the table 2. The mutants Y229 were constructed by overlap extension PCR using a QuickChange II-E Site-Directed Mutagenesis Kit (Stratagene) and primers MetY-forward (GCCAGTAAAGATAAGCGCTACGCCTTTGTGACGGG) (SEQ ID NO:35) and MetY-reverse (SEQ ID NO:36) complemented of forward primer.

TABLE 2

Sequences of the primers used in the construction of MetA mutants

| Primer | Mutation | Primer sequence |
|---|---|---|
| K3-forward | Q96K | AAGGATCAGAACTTTGACGGTTTG (SEQ ID NO: 19) |
| K3-reverse | Q96K | AATATCTTCAAAGTTACAGTAGAAG (SEQ ID NO: 20) |
| V3-forward | L110V | GGTGGGCCTGGTGGAGTTTAATG (SEQ ID NO: 21) |
| V3-reverse | L110V | GGCGCACCAGTTACAATCAAACC (SEQ ID NO: 22) |
| L2-forward | I124L | CAGCTCAAACAGGTGCTGGAGTG (SEQ ID NO: 23) |
| L2-reverse | I124L | CGGCCAGTAAGCGACATCATTAAAC (SEQ ID NO: 24) |
| L1-forward | R160L | CTCTCACCGAAAAACTCTCTGGC (SEQ ID NO: 25) |

TABLE 2-continued

Sequences of the primers used in
the construction of MetA mutants

| Primer | Mutation | Primer sequence |
|---|---|---|
| L1-reverse | R160L | TTTGCTTAGGAATGCCGTAGAGG (SEQ ID NO: 26) |
| T4-forward | A195T | CTATACTGACTTTCCGGCAGCGTTG (SEQ ID NO: 27) |
| T4-reverse | A195T | CGCGAATGCGGTGCCAGGAATGAATC (SEQ ID NO: 28) |
| E1-forward | A200E | CAGAGTTGATTCGTGATTACACCG (SEQ ID NO: 29) |
| E1-reverse | A200E | CCGGAAAGTCAGCATAGCGCGAATG (SEQ ID NO: 30) |
| G1-forward | D218G | GGTGCATATCTGTTTGCCAGTAAAG (SEQ ID NO: 31) |
| G1-reverse | D218G | CCCTTCTTCCGTCTCTGCCAGAATTTC (SEQ ID NO: 32) |
| Y2-forward | F247Y | GAATATTTCCGCGATGTGGAAGCC (SEQ ID NO: 33) |
| Y2-reverse | F247Y | CTGCGCCAGCGTTTGCGCATCATATTC (SEQ ID NO: 34) |

[a] - The mutation sites are in bold.

Cultivation of E. coli Strains in a Temperature Gradient Incubator.

Growth of E. coli strains in M9 glucose medium at different temperatures was studied using a temperature gradient incubator (TVS126MA, Adventec MSF Inc., USA). A single colony of each strain was cultivated in 5 ml M9 medium overnight at 30° C. The overnight cultures were diluted to $OD_{600}$ of 0.05 in 300 ml fresh M9 medium, dispensed into 15 ml tubes and incubated at 30-47° C. for 12 h with shaking. Growth was measured by monitoring the optical density at 600 nm every 5 min.

Purification of Aggregated and Soluble Proteins.

The metA chromosomal mutants of E. coli were grown in 75 ml M9 glucose medium in the flasks at 30° C. to mid-exponential phase (approx. $OD_{600}$ of 0.6). Twenty five ml of each culture were shifted to 45° C. for 40 min or treated with 30 mM acetic acid for 3 h at 30° C. The remaining 25 ml was used as a control. Aggregated and soluble protein fractions were purified as described previously (5, 19).

SDS-PAGE and Immunoblotting.

Gel electrophoresis was performed using 12% SDS-PAGE. After electrophoresis, the proteins were electroblotted on to nitrocellulose membranes (Bio-Rad, USA). MetA protein was detected using a rabbit anti-MetA serum raised against a synthetic oligopeptide consisting of 74-94 amino acids (2) of MetA (Peptron Inc., Korea) as primary antibody, and horseradish peroxidase-conjugated anti-rabbit IgG (Pierce, USA) as secondary antibody. The immunoblots were developed using a SuperSignal West Pico Chemiluminescent Substrate kit (Pierce, USA), scanned with Image Reader Fujufilm LAS-3000 and analyzed using LabWorks software.

Cloning, Expression and Protein Purification.

The wild-type and mutated metAs were cloned into NdeI/HindIII restriction sites of the plasmid pET22b in frame with a C-terminal 6×-histidine tag. The plasmid DNA was purified from ampicillin-resistant clones and sequenced to verify that the correct genes had been cloned. The resulting plasmids were transformed into competent E. coli BL21 (DE3) cells. A single colony of the strain E. coli BL21 (DE3) harboring the corresponding plasmid was cultivated overnight at 30° C. in 15 ml LB medium with ampicillin. Half a liter of 2×YT medium containing ampicillin was inoculated with an overnight culture, incubated at 30° C. to an $OD_{600}$ of 0.6, induced with IPTG (1 mM final concentration) and then cooled to 22° C. After 4 hrs induction, the cells were harvested by centrifugation and the pellets were resuspended in ice-cold buffer (50 mM Tris-HCl, 300 mM NaCl, 10 mM $MgCl_2$, 5 mM imidazole, pH 7.5) in the ratio 3 ml buffer/1 g of wet cells. The cells were lysed by incubation with 0.5 mg/ml lysozyme, 1 mM PMSF and DNase I for 30 min with stirring at 4° C., followed by sonication for 10×20 s with 20 s intervals using a Branson Sonifier (model 450). The cell debris was removed by centrifugation at 12000×g for 40 min. The proteins were purified from the supernatants using Ni-NTA agarose (Qiagen, USA). Two milliliters of agarose slurry was incubated with 6 ml supernatant overnight at 4° C. with rocking. The unbound proteins were removed by gravity filtration and the agarose was washed with 4 ml buffer (50 mM Tris-HCl, 300 mM NaCl, 100 mM imidazole, pH 7.5). The proteins were released from the agarose by elution with 6 ml buffer (50 mM Tris-HCl, 300 mM NaCl, 250 mM imidazole, pH 7.5) and the eluate was dialyzed against two changes of dialysis buffer (21, 50 mM K-phosphate buffer, 150 mM NaCl, pH 7.6) then against 50 mM K-phosphate buffer (pH 7.6) containing 150 mM NaCl and 50% glycerol for 6 h. The presence of pure protein in all the samples was confirmed by SDS-PAGE.

Measurement of Enzyme Activity.

Reaction rates were determined by monitoring the decrease in absorbance at 232 nm caused by hydrolysis of the thioester bond of succinyl-CoA (3) in a ND1000 UV/Vis Spectrophotometer (Nanodrop Technologies, USA). The assay solutions containing 50 mM K-phosphate buffer (pH 7.5), 200 µM succinyl-CoA, 5 mM L-homoserine, 1 µM of protein in a final volume of 20 µl were incubated for 30 min at 40, 45, 50, 55 and 58° C., or at 25° C. in the presence of acetic acid. L-homoserine was omitted from the control tubes. The reaction was started by adding the enzyme. The consumption of succinyl-CoA in the reaction was calculated as the difference between values obtained in the presence and absence of L-homoserine. Three independent measurements were performed for each point.

Differential Scanning Calorimetry.

The thermal stabilities of the MetAs were measured calorimetrically over the temperature interval 15-90° C. at a scan rate of 90° C./h. A VP-DSC calorimeter (MicroCal Inc., USA) was employed using 10 µM protein in 50 mM K-phosphate buffer (pH 7.5). Three scans were obtained from independent protein preparations.

Results

L-Methionine Stimulates E. coli Growth.

Figure 2:
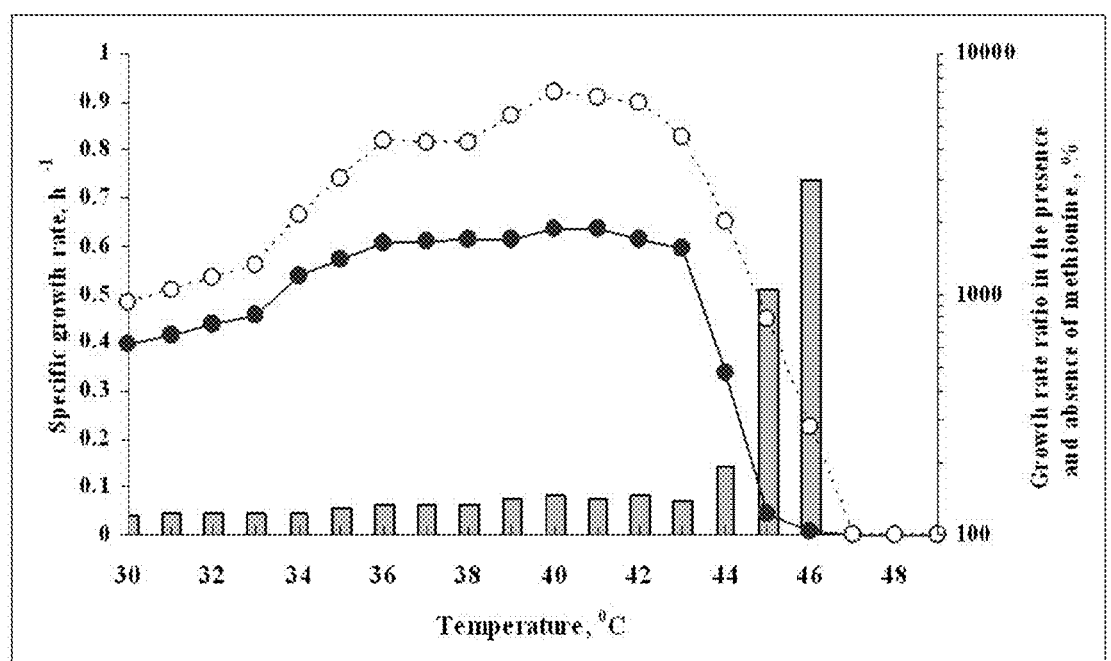
FIG. 2 shows the effect of methionine supplementation on the growth of *E. coli* strain W3110 at different temperatures. The strain was grown in M9 glucose minimal medium supplemented with (open circles) or without (closed circles) L-methionine in the temperature gradient incubator over the temperature range 30-49° C. Columns indicate the ratio of specific growth rates between methionine-enriched (50 µg ml$^{-1}$) and methionine-deficient media.

To confirm the stimulatory effect of methionine on E. coli growth at elevated temperatures, strain W3110 was cultivated in M9 glucose medium in the temperature range 30-49° C. with or without L-methionine (50 µg $ml^{-1}$) in the temperature gradient incubator. Methionine accelerated E. coli growth at temperatures over 30° C. (FIG. 2). E. coli strain W3110 grew very slowly without methionine at 45° C. and completely ceased to grow at 46° C. or over (FIG. 2), confirming previous findings (16). Supplementation of the culture medium with methionine allowed growth at 45° C.

and 46° C., but no growth was detected over 47° C. (FIG. 2). Expectedly, the methionine effect was more prominent at higher growth temperatures: the specific growth rate was increased two-fold at 44° C. and 10-fold at 45° C. (FIG. 2).

MetA from the Thermophilic Strain *Geobacillus kaustophilus* Accelerates *E. coli* Growth at Elevated Temperature.

Figure 4:
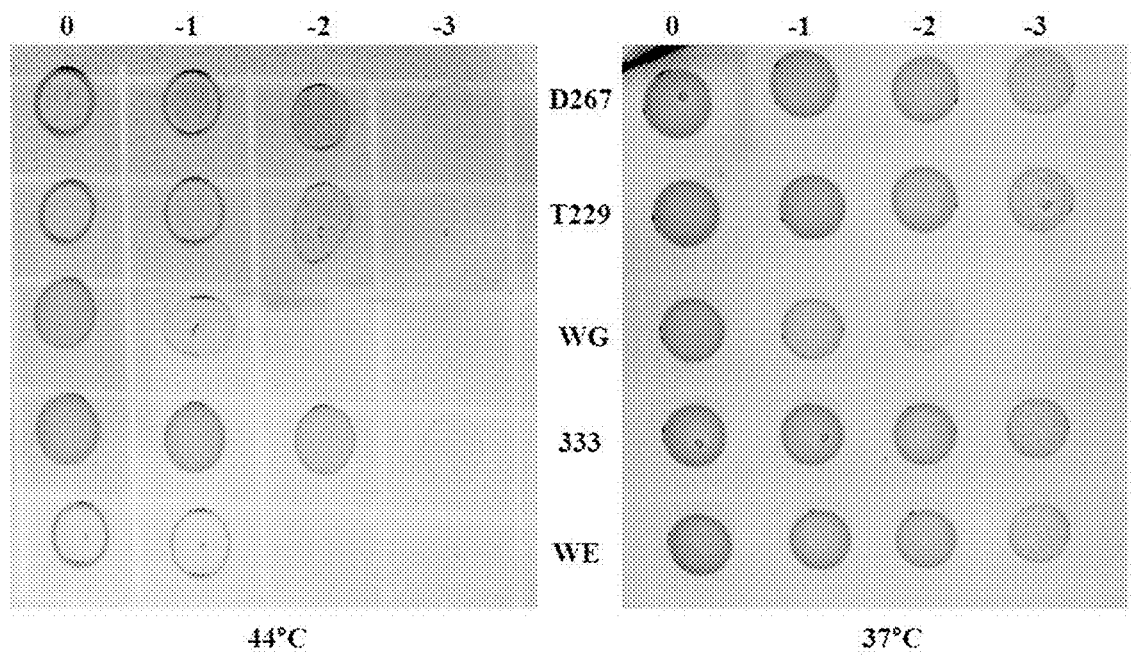
FIG. 4 shows thermostability of *E. coli* metA mutants. Samples were taken from logarithmically growing cultures at 30° C. in M9 glucose medium, adjusted to equal density, serially diluted in M9 medium (no glucose). Aliquots (5 µl) were spotted on M9 glucose plates. Cells were incubated for 24 hrs at the indicated temperatures.

We checked whether MetA from the thermophilic strain would simply improve *E. coli* growth at higher temperature. As a thermostable gene we used metA from the strain *G. kaustophilus* KCTC 3397. This is an aerobic gram-positive endospore-forming bacterium which can grow at 37-75° C. with an optimum 55-65° C. (21). The metA$_{Geo}$ was cloned under the *E. coli* metAp on the pPmetA plasmid. The resulting plasmid, pGeo-metA, compensated the growth of the metA-null mutant on M9 medium. However, the specific growth rate of *E. coli* strain JW3973 (pGeo-MetA) was 20% less than that of *E. coli* JW3973 (pMetA) at 37° C. We integrated metA$_{Geo}$ into the *E. coli* chromosome to yield the strain WG. The metA$_{Geo}$ stimulated *E. coli* growth on solid M9 medium at 44° C. (FIG. 4).

Directed Evolution of MetA Results in Thermotolerant *E. coli* Strains.

Figure 3:
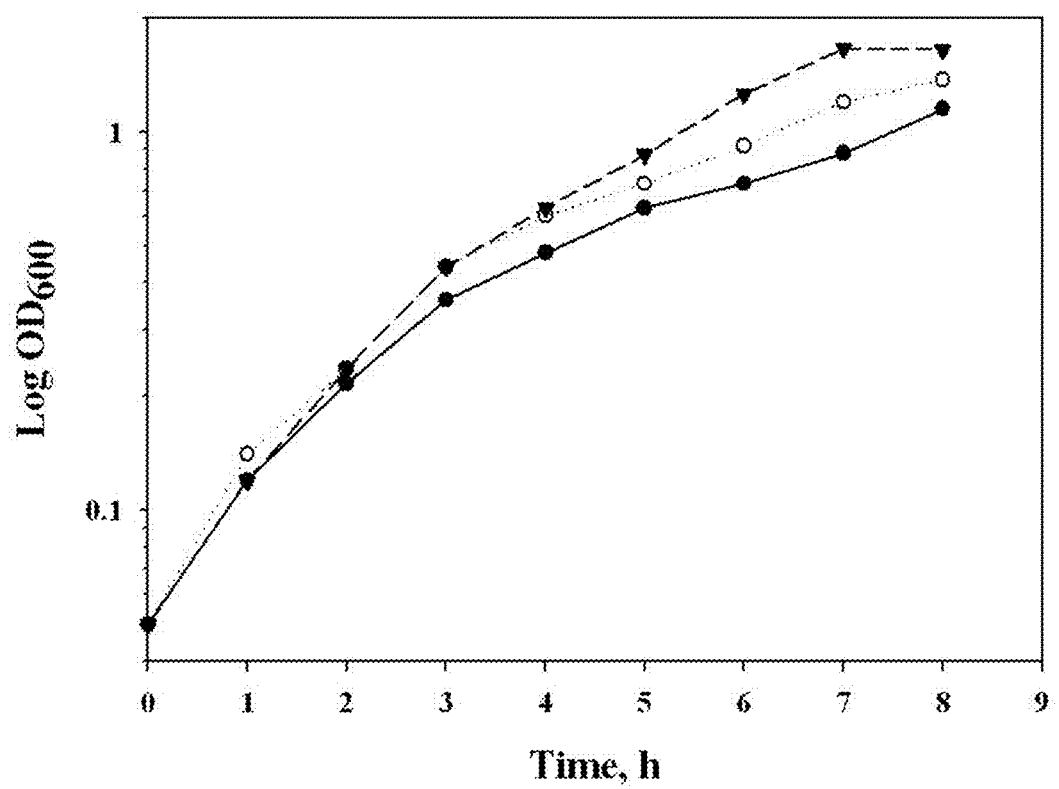
FIG. 3 represents the selection of the thermostable MetA$_{E.coli}$-333 from the library of metA$_{E.coli}$ mutants. Cultures of 23 strains *E. coli* JW3973 harboring the plasmid pMetA with mutated metA$_{E.coli}$s and non-mutated control were flask-cultivated in M9 glucose medium at 44° C. The optical density was measured at 600 nm every 1 hr. Symbols: pMetA-control, ●; pMetA-333, ▼; pMetA-334, ○. The growth curves of other metA$_{E.coli}$ mutants are similar to control strain.

As methionine and thermostable MetA$_{Geo}$ relieve the impairment of *E. coli* growth at higher temperatures, we tried to obtain a more thermostable MetA$_{E.coli}$ by monitoring the enhancement of growth of *E. coli* cells carrying mutant metA$_{E.coli}$ at higher temperatures. We supposed that thermostable MetA$_{E.coli}$ might accelerate the *E. coli* growth not only at elevated but at mild temperatures in contrast to MetA$_{Geo}$ lowering the specific growth rate of *E. coli* at 37° C. Random mutagenesis of metA$_{E.coli}$ was performed with error-prone PCR as described in Materials and Methods. We constructed a library of mutated metAs into the pPmetA plasmid that completely restored growth of the metA null mutant *E. coli* JW3973 on M9 glucose medium. The library, consisting of 490 clones, was incubated on M9 minimal plates at 44° C. to select the growing clones. Twenty-three selected clones were then cultivated in liquid M9 glucose medium at 44° C. to identify the most rapidly-growing one. One prospective clone, which grew faster than the others at the elevated temperature, was designated strain 333 (FIG. 3). Sequencing showed the presence of five amino acid substitutions—S61T, E213V, I229T, N267D and N271K—in MetA$_{E.coli}$-333. To determine which amino acid residue is responsible for the improved thermostability, single amino acid substitutions corresponding to those found in MetA$_{E.coli}$-333 were introduced into the wild-type enzyme by site-directed mutagenesis. We integrated all the mutated metA$_{E.coli}$ genes into the *E. coli* JW3973(ΔmetA) chromosome to yield strains 333, T61, V213, T229, D267 and K271. To study the thermostabilities of these metA mutants, we cultivated them on solid M9 glucose plates at 44° C. In FIG. 4, the left panel shows that the control strain WE, which harbors non-mutated metA on the chromosome, weakly grew at 44° C., in contrast to the mutants 333 and WG. Among the single mutants only two strains, T229 and D267, grew better than the control strain at the elevated temperature (FIG. 4). All the strains grew normally at 37° C. (FIG. 4, right panel) except the WG, which grew more slowly than the others.

Thermotolerant *E. coli* metA Mutants Grow Faster at Elevated Temperatures.

Figure 5:
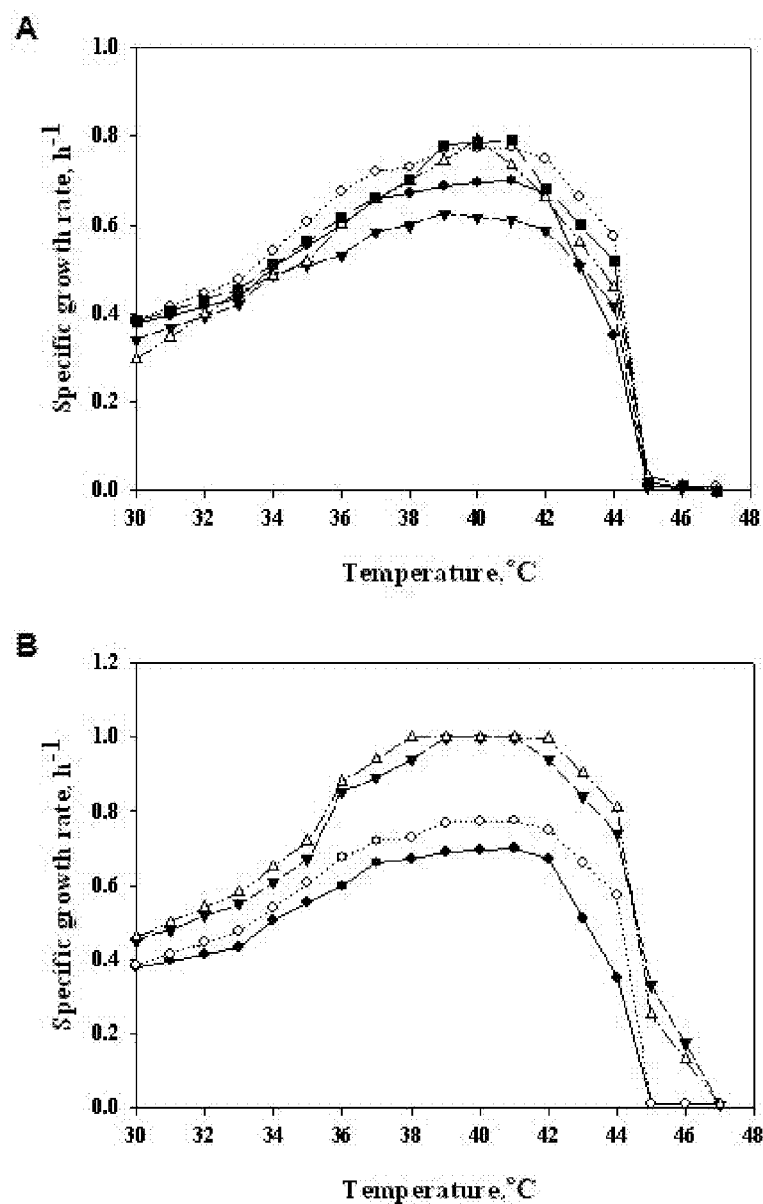
FIG. 5 represents the effect of different temperatures (A) and methionine supplementation (B) on growth of *E. coli* metA mutants. Non-mutated and mutated metAs were integrated into the chromosome of the *E. coli* strain JW3973 instead of the kanamycin resistance gene. The strains were grown in M9 glucose medium in the temperature gradient incubator over the temperature range 30-47° C. for 12 hrs. Methionine was added to a final concentration of 50 µg ml$^{-1}$. Symbols (A): WE, ●; 333, ○; WG, ▼; D267, Δ; T229, ■. Symbols (B): WE, ●; 333, ○; WE+methionine, ▼; 333+methionine, Δ.

To study the growth of thermostable mutants at different temperatures we cultivated them in a temperature gradient incubator. The results presented in FIG. 5A show that the strains 333 grew 5-12% faster than the non-mutated strain WE over the temperature range 30-42° C. However, the difference in specific growth rate between the thermostable strain 333 and the control strain WE increased to 30% at 43° C. and to 64% at 44° C. (FIG. 5A). The single-mutated metA strains T229 and D267 grew 48 and 31% faster at 44° C., and 18 and 10% faster at 43° C., respectively. In the temperature range 39-41° C. the difference in specific growth rate between single-site mutants and control strain decreased to 4-12% and fell to zero over the range 30-38° C. (FIG. 5A). No growth was detected at 45° C. or over for any strains tested.

The foreign metA$_{Geo}$ lowered host strain growth in liquid M9 medium at mild temperatures, 30-42° C., by approximately 10% (FIG. 5A). At 43° C. the specific growth rate of WG was the same as for the control strain WE, and at 44° C. it grew 20% faster than the control strain (FIG. 5A).

We also cultivated the other single-site mutants at different temperatures. Two of them, V213 and K271, had lower specific growth rates than wild type at 44° C. (64% and 22% of control strain) (data not shown), but grew 15-20% faster than the non-mutated strain at 36-41° C. (data not shown). The single-site mutant T61 grew as the wild-type at elevated temperatures, but its specific growth rate at 36-41° C. was similar to the mutants V213 and K271 (data not shown). Apparently, the multiple metA mutant 333 combined the abilities of the thermosensitive mutants to accelerate the growth at mild temperatures and of the thermostable mutants to grow faster at higher temperatures.

In order to ascertain the influence of methionine on growth of the thermostable *E. coli* 333 strain, we cultivated these strains with or without methionine at different temperatures using the non-mutated WE strain as a control (FIG. 5B). Despite the presence of the thermostable MetA$_{E.coli}$-333, this mutant could not attain the specific growth rate obtained in the presence of methionine. However, although the non-mutated strain grew 1.6 and 2 times slower in methionine-deficient medium at 43 and 44° C., respectively, the thermostable variant decreased this difference to 1.4-fold at both temperatures. This is apparently because another thermolabile protein is present in the methionine biosynthesis pathway. Previous investigations have shown that MetE, which catalyzes the final step in methionine biosynthesis, is also sensitive to elevated temperature (9).

Thermostable metA Mutants are Tolerant to Acetic Acid.

Figure 6:
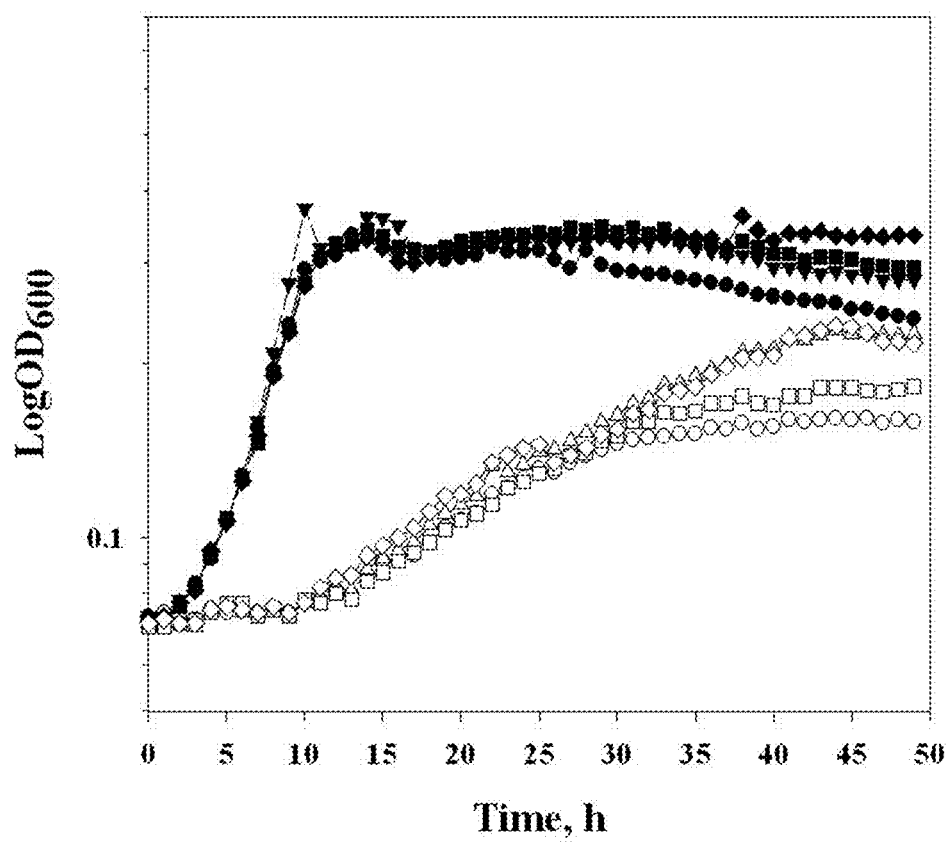
FIG. 6 shows influence of acetic acid on the growth of thermostable *E. coli* mutants. The strains were cultivated in 100 µl M9 glucose medium at 30° C. in the BioScreen C incubator for 49 hrs with 15 min intervals of shaking in the presence of 30 mM acetic acid (open symbols) or without it (solid symbols). Symbols: WE, circles; 333, triangles; D267, squares; T229, diamonds.

Since it is known that weak organic acids can destabilize MetA$_{S.enterica}$ (11), we supposed that thermostable metA mutants might also be resistant to acetic acid. The strains 333, D267, T229 and WE were cultivated in M9 glucose medium supplemented with 30 mM acetic acid at 30° C. in the BioScreen C incubator (Labsystems, Finland). As shown in FIG. 6, the wild-type strain reached stationary phase 29 h after the beginning of cultivation. In contrast, the thermostable *E. coli* strains 333 and T229 grew intensively for a further 11 h and achieved a 1.4 times greater cell density than the control strain. Another mutant, D267, grew slower than other thermostable strains, and its cell density was only 16% more than control.

Thermostable MetA Enzymes are Less Susceptible to Aggregation In Vivo Under Heat or Acetic Acid Stress Conditions.

Figure 7:
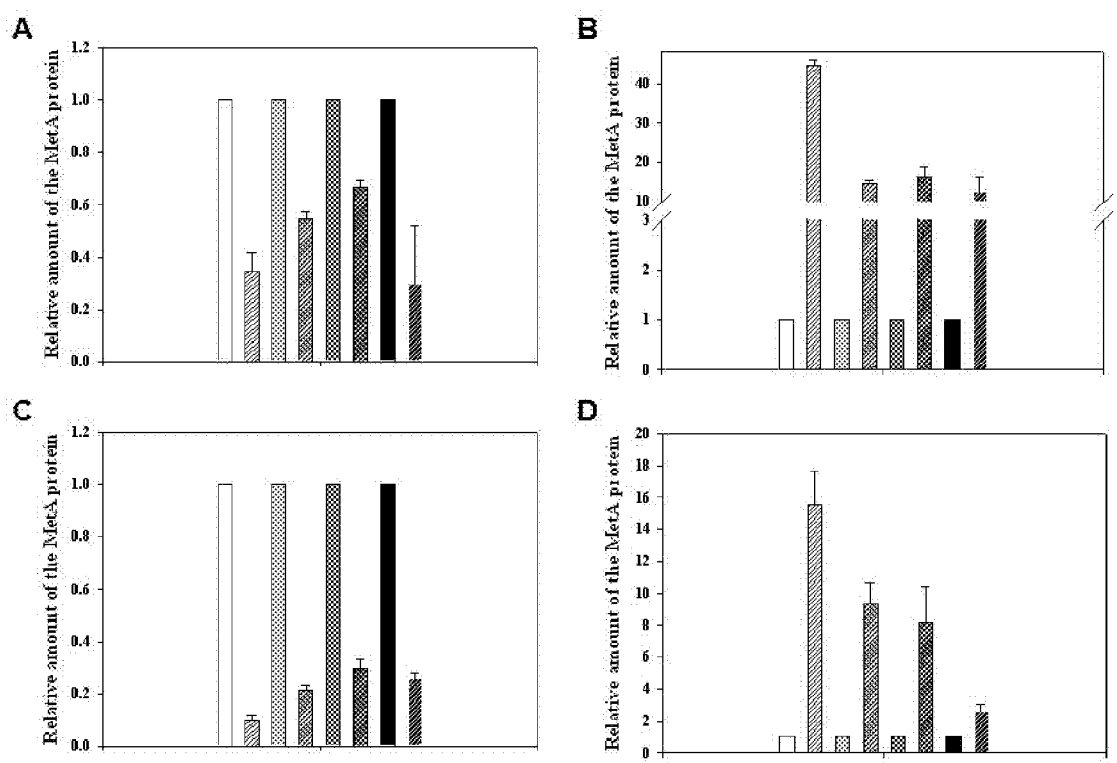
FIG. 7 represents the densitometric analysis of MetAs in heat (A, B) or acetic acid stressed (C, D) cultures. The strains WE (white columns), 333 (gray columns), D267 (dark gray columns), and T229 (black columns) were grown in M9 glucose medium to exponential phase (approx. OD$_{600}$=0.6) at 30° C. and were then shifted to 45° C. for 40 min or incubated in the presence of 30 mM acetic acid for 3 hrs at 30° C. Soluble (A, C) and aggregated (B, D) fractions of MetAs were purified from 25 ml cultures as described in Materials and Methods. Three µg of total protein were loaded on 12% SDS-PAGE followed by Western blotting using rabbit anti-MetA serum. MetAs were quantified by densitometry using LabWorks software and normalized to the total amount of protein. MetAs from the unstressed cultures were equaled to 1 (plain columns). An average of two independent experiments is presented.

To determine the effect of elevated temperature or acetic acid treatment on thermostable MetA$_{E.coli}$ proteins in vivo, the mutant and control strains were heated from 30° C. to 45° C. for 40 min or incubated with 30 mM acetic acid for 3 h at 30° C., and the relative amount of MetA$_{E.coli}$ was evaluated by immunoblotting. Biran and coworkers (2) showed that *E. coli* cells contain no soluble MetA$_{E.coli}$ at temperatures above 44° C. Surprisingly, we found wild-type MetA$_{E.coli}$ protein in the soluble fraction after the heat stress; its level was about 35% of that in an unstressed culture (FIG. 7A). Perhaps part of the unfolded MetA$_{E.coli}$ protein partitioned into the soluble fraction. The relative amounts of the soluble thermostable MetA$_{E.coli}$-333 and MetA$_{E.coli}$-D267 proteins were 58% and 67% (FIG. 7A). In contrast, soluble MetA$_{E.coli}$-T229 protein at 45° C. was only 29% of that in the unheated control (FIG. 7A). The relative content of insoluble non-mutated MetA$_{E.coli}$ protein increased 44 times after heating (FIG. 7B). The insoluble fractions of all the mutants tested were only 13-19 times more abundant after high-temperature treatment than in unheated cultures (FIG. 7B). The data obtained in this experiment confirmed that the MetA$_{E.coli}$-333 and MetA$_{E.coli}$-D267 mutants are more resistant in forming aggregates after a heat challenge. For MetA$_{E.coli}$-T229, we assume that resistance to aggregation is greater because of a more stable protein secondary structure.

Acetic acid challenge of exponentially growing cultures produced a relative level of soluble MetA$_{E.coli}$ 1.5-3 times higher in all the mutants tested than in the wild-type strain (FIG. 7C). The insoluble MetA$_{E.coli}$ content was approximately 15 times greater in the wild-type strain, 8-9 times in the D267 and 333 strains, and 2.6 times in the T229 strain (FIG. 7D). These results confirm that the mutated MetA$_{E.coli}$ proteins are more resistant in forming aggregates than the wild-type protein when challenged with acetic acid.

Thermostable MetA Enzymes have Increased Transition Midpoints.

Figure 8:
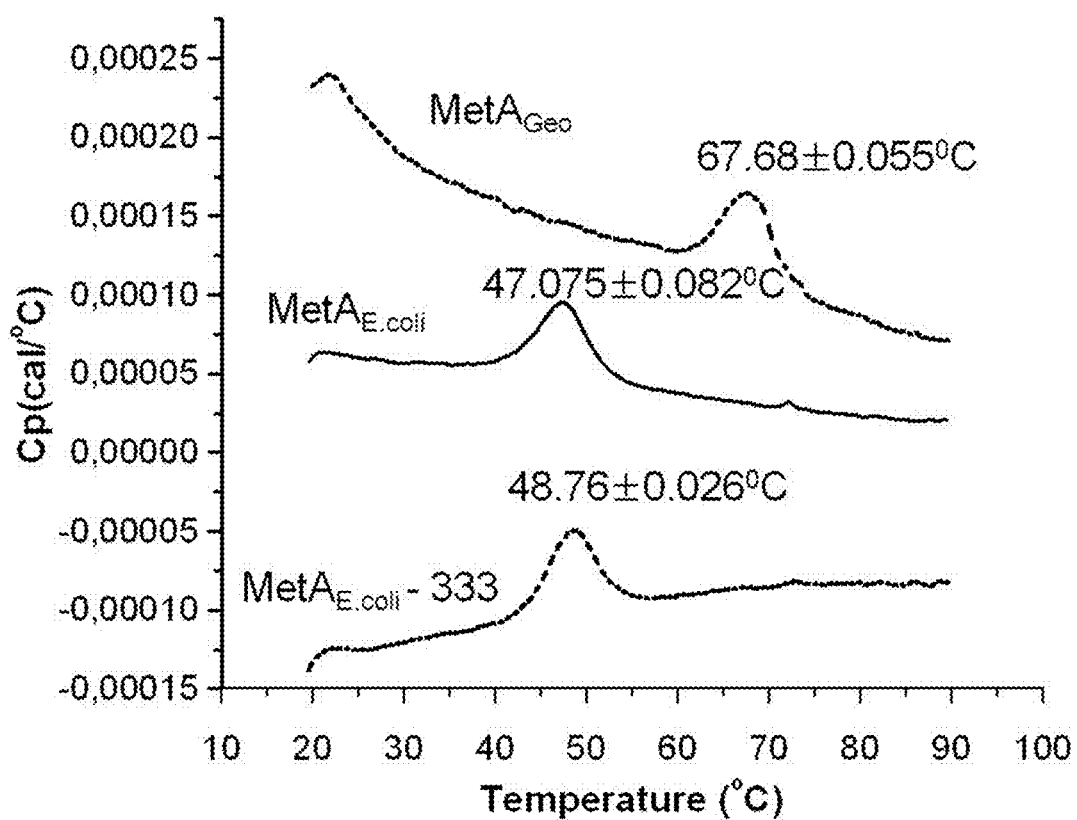
FIG. 8 is thermograms of his-tagged MetAs obtained by differential scanning microcalorimetry. All the proteins were scanned as described in Materials and Methods. The Tm indicated above the corresponding curve is the midpoint of the unfolding transition in differential scanning microcalorimetry; it was determined from three independent experiments.

Differential scanning calorimetry (DSC) was used to compare the transition midpoint (Tm) of mutated and wild-type MetA proteins. Tm is an indicator of thermostability, and proteins with higher Tm are less susceptible to unfolding and denaturation. Non-mutated and mutated MetAs containing a C-terminal 6×-histidine tag were purified as described in Materials and Methods. As shown in FIG. 8, the wild-type 6-his-tagged MetA$_{E.coli}$ had a Tm at 47.075±0082° C., while MetA$_{E.coli}$-333 had a higher Tm (48.76±0.026° C.) (FIG. 8). The highest Tm (67.68±0.055° C.) was found for MetA$_{Geo}$ (FIG. 8). Although the single-site mutated proteins MetA$_{E.coli}$-D267 and MetA$_{E.coli}$-T229 stimulated E. coli growth at elevated temperatures, they had Tm values very close to that of wild-type MetA$_{E.coli}$ (47.36±0.014° C. and 46.99±0.063° C., respectively). Maybe these mutant enzymes are not more stable than wild type but more resistant in forming aggregates after heat challenge. This possibility will be investigated in a near future.

Mutated MetA Enzymes have Enhanced Activities at Elevated Temperatures and in the Presence of Acetic Acid.

Figure 9:
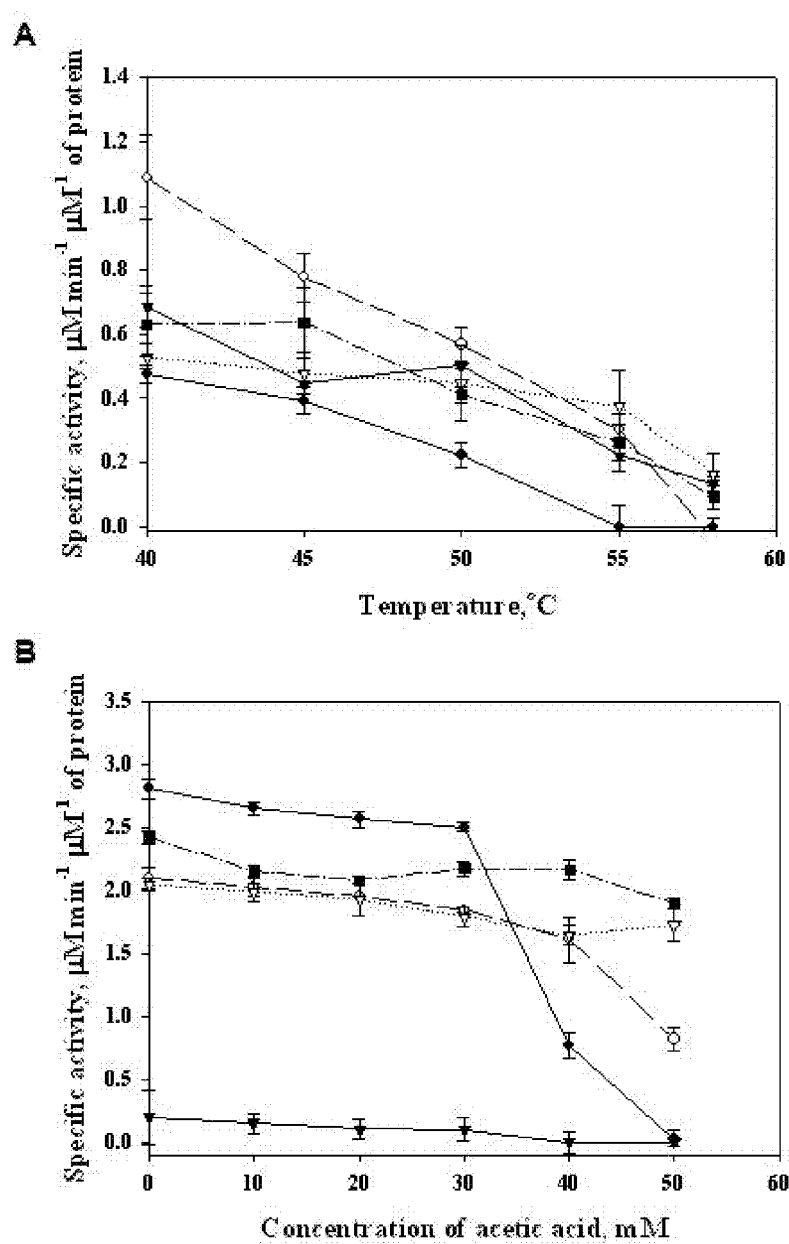
FIG. 9 represents temperature dependence (A) and acetic acid tolerance (B) of his-tagged MetAs. The activities of non-mutated MetA$_{E\,coli}$ and MetA$_{Geo}$, and mutated MetA$_{E\,coli}$ proteins were measured by monitoring the decrease in absorbance at 232 nm caused by hydrolysis of the thioester bond of succinyl-CoA, the substrate for MetA, over the temperature range 40-58° C. (A), and at 25° C. in the presence of acetic acid (B). An average of three independent measurements is presented for each point. Symbols: MetA$_{E\,coli}$, ●; MetA$_{E\,coli}$-333, ○; MetA$_{Geo}$, ▼; MetA$_{E\,coli}$-D267, ∇; MetA$_{E\,coli}$-T229, ■.

The activities of the 6×-histidine tagged MetA enzymes purified as described in Materials and Methods were measured at temperatures between 40 and 58° C. by monitoring the change in absorbance at 232 nm due to hydrolysis of the succinyl-CoA thioester bond. The data obtained for the thermostable MetA proteins are presented in the top panel of FIG. 9. MetA$_{E.coli}$-333 was approximately 2.5 times more active than the non-mutated protein at 40-55° C. but completely lost its activity at 58° C. In contrast to MetA$_{E.coli}$-333, MetA$_{Geo}$, MetA$_{E.coli}$-D267 and MetA$_{E.coli}$-T229 displayed the lower activities at 40-45° C. but at 50° C. and higher the temperature profiles of all thermostable MetAs were similar. Surprisingly, the catalytic activity of MetA$_{Geo}$, gradually decreased at elevating temperatures, perhaps because of the thermal instability of succinyl-CoA.

We tested the catalytic activity of the mutated MetAs in the presence of acetic acid at 25° C. Acetic acid in a final concentration of 10 mM lowered the pH of reaction buffer from 7.5 to 7.0; 20 mM-to pH 6.6; 30 mM-to pH 6.2; 40 mM-to pH 5.8; 50 mM-to pH 5.4. FIG. 9B shows that the activity of wild-type MetA$_{E.coli}$ decreased sharply when the acetic acid concentration raised over 30 mM (pH 6.2), and was not detectable at 50 mM (pH 5.4). Our findings confirmed the earlier investigations that the wild-type MetA$_{E.coli}$ activity significantly dropped over pH range of 6.0-6.5 (3). Acetic acid also inhibited the activity of MetA$_{E.coli}$-333 starting from 30 mM, but somewhat less severely than the wild-type enzyme. Moreover, MetA$_{E.coli}$-333 remained active in 50 mM acetic acid (FIG. 9B). Two other enzymes, MetA$_{E.coli}$-D267 and MetA$_{E.coli}$-T229, had unchanged catalytic activities at all the acetic acid concentrations tested (FIG. 9B). Interestingly, MetA$_{Geo}$ was almost inactive at 25° C. (FIG. 9B).

Consequently, we compared the catalytic activities of the wild-type MetA$_{E.coli}$, and thermostable MetA$_{E.coli}$ mutant enzymes at 25 and 40° C. (FIGS. 9A and B). The wild-type enzyme activity was 80% lower at 40° C. In contrast, MetA$_{E.coli}$-333 was 50% less active at 40° C., while MetA$_{Geo}$ was 3.5 times more active at the elevated temperature (FIGS. 9A and B). These results of wild-type enzymes are consistent with previous findings; the activity of MetA$_{E.coli}$ decreased by 70% at 37° C. and 42° C. (14).

Single-Mutated MetAs' Stimulates E. Coli Growth at Elevated Temperature.

In order to extend the mutation study of the MetA$_{E.coli}$, we performed the multiple alignment of MetA amino acid sequences from E. coli and thermophilic bacteria (FIG. 10). As a result, we found eight amino acid residues presented in all the thermophilic MetAs' but not in MetA$_{E.coli}$ (FIG. 10). To determine which amino acid residue might increase the MetA$_{E.coli}$ thermostability, single amino acid substitutions—Q96K, L110V, I124L, R160L, A195T, A200E, D218G and F247Y—were introduced into wild-type enzyme by site-directed mutagenesis. We integrated all of the mutated metA$_{E.coli}$ genes into E. coli JW3973 (ΔmetA) chromosome to yield strains K96, V110, L124, L160, T195, E200, G218 and Y247. To study the thermostability of these single-site metA$_{E.coli}$ mutants, we cultivated them in liquid M9 glucose medium at 44° C. The results presented in Table 3 show that five mutants K96, V110, L124, E200, and Y247 grew faster at elevated temperature in contrast to control strain WE. The cultivation of five thermostable metA mutants at mild temperatures 32 and 37° C. did not reveal any differences between them and nonmutated WE strain (Table 3). What is surprising is that other three single-site metA mutations did not maintain the E. coli growth at elevated temperature but significantly decreased the specific grow rate at 37° C. at 50%-G218, at 32%-L160, at 17%-T195 (Table 3). All the thermosensitive mutants also grew slower at 32° C. than the control strain (Table 3).

Earlier, we obtained the thermostable T229 mutant harboring I229T substitution. Using the program, we determined that the replacement of isoleucine with tyrosine might additionally increase the MetA$_{E.coli}$ protein stability. The single-site mutant Y229 also revealed an accelerated growth at 44° C. (Table 3) but not higher than another mutant T229 (data not shown).

TABLE 3

Effect of single amino acid substitutions in metA gene on the E. coli growth at different temperatures.

| Name of mutant | Mutation | Specific growth rate μ, h$^{-1a}$ | | |
|---|---|---|---|---|
| | | at 32° C. | at 37° C. | at 44° C. |
| WE | Wild-type | 0.43 ± 0.007 | 0.59 ± 0.01 | No growth |
| K96 | Q96K | 0.48 ± 0.007▲ | 0.58 ± 0.007 | 0.52 ± 0.007▲ |
| V110 | L110V | ND | 0.55 ± 0.008 | 0.19 ± 0.07▲ |
| L124 | I124L | 0.46 ± 0.007 | 0.6 ± 0.06▼ | 0.51 ± 0.02▲ |
| L160 | R160L | 0.37 ± 0.014▼ | 0.4 ± 0.03▼ | No growth |
| T195 | A195T | 0.37 ± 0.007▼ | 0.49 ± 0.007▼ | No growth |
| E200 | A200E | ND | 0.56 ± 0.014 | 0.37 ± 0.09▲ |
| G218 | D218G | 0.36 ± 0.004▼ | 0.29 ± 0.03▼ | No growth |
| Y229 | I229Y | 0.45 ± 0.014 | 0.61 ± 0.024 | 0.31 ± 0.1▲ |
| Y247 | F247Y | ND | 0.6 ± 0.007 | 0.1 ± 0.03▲ |

The growth experiments were performed by flask cultivation in minimal M9 medium. A single colony of each strain was cultivated in 5 ml M9 medium overnight at 30° C. The overnight cultures were diluted to OD$_{600}$ of 0.1 in 25 ml fresh M9 medium and incubated at 32, 37 or 44° C. with shaking. Growth was measured by monitoring the optical density at 600 nm every 1 h.
$^a$Specific growth rate was calculated as In (X/X$_0$) where X$_0$ and X are OD$_{600}$ values in zero time point and 1 h afterward for an exponentially growing culture.
Symbols:
▼decrease of specific growth rate is ≥10% of control strain;
▲increase of specific growth rate is ≥10% of control strains;
ND—not determined.

Discussion

The unusual instability of MetA, the first enzyme in the methionine biosynthesis pathway, is the main factor limiting E. coli growth at elevated temperatures (2, 5, 13, 14, 15). MetA$_{E.coli}$ activity is reduced at temperatures higher than 33° C. due to the formation of aggregates (2). As addition of methionine or replacing with thermostable MetA relieved the growth inhibition at higher temperatures, directed evolution of the MetA$_{E\ coli}$ should widen the temperature range over which E. coli strains can grow. Using directed evolution, we obtained the thermotolerant enzyme MetA$_{E.coli}$-333 with five the amino acid substitutions (S61T, E213V, I229T, N267D and N271K), which accelerates the growth of the host strain not only at higher temperatures but also at normal growth temperature 37° C. The higher thermostability of MetA$_{E.coli}$-333 was confirmed in vivo by the differential scanning calorimetry data, and higher activity was demonstrated at elevated temperatures. MetA$_{E.coli}$-333 was also classified as stable using ProtParam software (http://ca.expasy.org/): it has an instability index of 39.79, in contrast to the wild-type MetA$_{E\ coli}$, which has an instability index of 42.26. The instability index provides an estimate of the protein stability. A protein whose instability index is smaller than 40 is predicted as stable, a value above 40 predicts that the protein may be unstable (6).

Accelerated growth of the single-site metA$_{E.coli}$ mutants at 44° C. allowed the identification of critical amino acid residues involved in the thermal instability of MetA$_{E.coli}$. Substitution of asparagine-267 with aspartic acid was expected to increase thermostability because the MetA proteins known from thermophilic strains carry a positively charged amino acid in this position (FIG. 1). In general, this finding confirms the earlier observation that proteins from thermophiles contain more charged amino acid residues than those from mesophiles (18). The substitution of isoleucine-229 with threonine is an 'opposite' case: theoretically, it would not be expected to increase the thermostability of MetA because proteins from thermophilic strains usually contain lower levels of polar amino acids (18). Secondary structure prediction for MetA$_{E.coli}$ (see World Wide Web (www) igb.uci.edu) showed that isoleucine-229 belongs to one of the beta strands. Several beta strands connected laterally by three or more hydrogen bonds generally form a twisted, pleated sheet (20). Association among beta sheets has been implicated in the formation of protein aggregates and fibrils observed in many human diseases, notably the amyloidoses (10). We assume that the substitution of isoleucine-229 with threonine lowers the beta strand length (see World Wide Web (www) igb.uci.edu) and decreases the capacity of MetA$_{E.coli}$ to aggregate under stress conditions. These mutant enzymes may improve the growth of E. coli at higher temperatures not because they became more thermostable but because they became more resistant in forming aggregates after heat challenge.

Biran and coworkers (2) attempted to stabilize MetA$_{E.coli}$. They showed that the amino-terminal part of the protein (first 23 amino acids) was responsible for its instability, and assumed that this sequence constituted a proteolytic site, or a binding site for proteins that might convert MetA$_{E\ coli}$ into a proteolytic substrate (2). On the basis of this investigation, we supposed that thermostable MetA$_{E\ coli}$ might carry mutations in the N-terminal region. However, the thermostable MetA$_{E.coli}$-333 mutant harbored no amino acid substitutions in that region.

Quite notably, thermostable E. coli MetAs were more resistant to acetic acid in vivo than the wild-type protein. In previous investigations it has been shown that methionine relieves the inhibition of E. coli growth by acetic acid (7, 12). Extended exponential growth of the metA$_{E.\ coli}$ mutants in the presence of acetic acid might serve as additional evidence of their increased acid tolerance because mid-exponential phase cultures were found to be more acid-sensitive than stationary phase cultures (1). Price-Carter and coworkers found that MetA from Salmonella enterica was as unstable at elevated temperature as in the presence of weak organic acids including acetate, benzoate, and propionate (11). Earlier, Roe and coworkers (12) concluded that inhibition of E. coli growth by acetate treatment was due to accumulation of homocysteine, the substrate of MetE. We assume that instability in both these enzymes may affect E. coli growth under stress conditions of heat and acetic acid.

In this study, we showed that methionine stimulates E. coli growth not only at elevated temperatures (42-46° C.) but also under normal growth temperature (37° C.). The thermotolerant MetA$_{E.coli}$-333 significantly increased growth rate of host strain at 44° C. but did not rescue it at 45° C. The same effect was found in the strain WG, which harbors a metA from the thermophilic bacterium G. kaustophilus. Supplementation with methionine produces additional E. coli growth at 45° and 46° C., indicating that there would be at least one more thermosensitive enzyme in the methionine biosynthesis pathway. We suppose that MetE, which catalyzes the final step in methionine biosynthesis, is a candidate because MetE has been shown to be sensitive to high-temperature (9) and oxidative stress (8).

This paper describes the first experimental demonstration that E. coli growth is accelerated under normal and stress conditions by increasing the stability of a single cytosolic enzyme, MetA. This study paves the way to obtaining a new platform E. coli strains growing at higher speed at normal growth temperature, thus potentially improving the productivity of microbial factory. More directly, being able to grow E. coli cells at higher temperatures means a reduced cooling, which is a considerable cost factor in bioprocesses.

REFERENCES

1. Arnold, K. W., and C. W. Kaspar. 1995. Starvation- and stationary phase-induced acid tolerance in Escherichia coli O157:H7. Appl. Environ. Microbiol. 61: 2037-2039.

2. Biran, D., E. Gur, L. Gollan, and E. Z. Ron. 2000. Control of methionine biosynthesis in *Escherichia coli* by proteolysis. Mol. Microbiol. 37: 1436-1443.
3. Born, T. L., and J. S. Blanchard. 1999. Enzyme-catalyzed acylation of homoserine: Mechanistic characterization of the *Escherichia coli* metA-encoded homoserine transsuccinylase. Biochemistry 38: 14416-14423.
4. Datsenko, K., and B. L. Wanner. 2000. One-step inactivation of chromosomal genes in *Escherichia coli* K-12 using PCR products. Proc. Natl. Acad. Sci. USA 97: 6640-6645.
5. Gur, E., D. Biran, E. Gazit, and E. Z. Ron. 2002. In vivo aggregation of a single enzyme limits growth of *Escherichia coli* at elevated temperature. Mol. Microbiol. 46: 1391-1397.
6. Guruprasad, K., B. V. B. Reddy, and M. W. Pandit. 1990. Correlation between stability of a protein and its dipeptide composition: a novel approach for predicting in vivo stability of a protein from its primary sequence. Protein Eng. 4: 155-161.
7. Han, K., J. Hong, and H. C. Lim. 1993. Relieving effects of glycine and methionine from acetic acid inhibition in *Escherichia coli* fermentation. Biotechnol. Bioeng. 41:316-324.
8. Hondorp, E. R., and R. G. Matthews. 2004. Oxidative stress inactivates cobalamin-independent methionine synthase (MetE) in *Escherichia coli*. PLoS Biol. 2: 1738-1753.
9. Mogk, A., T. Tomoyasu, P. Goloubinoff, S. Rüdiger, D. Röder, H. Langen, and B. Bukau. 1999. Identification of thermolabile *Escherichia coli* proteins: Prevention and reversion of aggregation by DnaK and ClpB. EMBO J. 18: 6934-6949.
10. Nelson, R, M. R. Sawaya, M. Balbirnie, A. O. Madsen, C. Riekel, R. Grothe, and D. Eisenberg. 2005. Structure of the cross-beta spine of amyloid-like fibrils. Nature 435: 773-778.
11. Price-Carter, M., T. G. Fazzio, E. I. Vallbona, and J. R. Roth. 2005. Polyphosphate kinase protects *Salmonella enterica* from weak organic acid stress. J. Bacteriol. 187: 3088-3099.
12. Roe, A. J., C. O'Byrne, D. McLaggan, and I. R. Booth. 2002. Inhibition of *Escherichia coli* growth by acetic acid: a problem with methionine biosynthesis and homocysteine toxicity. Microbiology 148: 2215-2222.
13. Ron, E. Z., and B. D. Davis. 1971. Growth rate of *Escherichia coli* at elevated temperatures: limitation by methionine. J. Bacteriol. 107: 391-396
14. Ron, E. Z., and M. Shani. 1971. Growth rate of *Escherichia coli* at elevated temperatures: reversible inhibition of homoserine trans-succinylase. J. Bacteriol. 107: 397-400.
15. Ron, E. Z. 1975. Growth rate of Enterobacteriaceae at elevated temperatures: limitation by methionine. J. Bacteriol. 124: 243-246.
16. Ron, E. Z., S. Alajem, D. Biran, and N. Grossman. 1990. Adaptation of *Escherichia coli* to elevated temperatures: The metA gene product is a heat shock protein. Antonie van Leeuwenhoek 58: 169-174.
17. Sambrook, J, E. F. Fritsch, and T. Maniatis. 1989. Molecular cloning: A laboratory manual. 2nd ed. Cold Spring Harbor Laboratory Press. Cold Spring, N.Y.
18. Scandurra, R. V, V. Consalvi, R. Chiaraluce, L. Politi, and P. C. Engel. 2000. Protein stability in extremophilic archaea. Front. Biosci. 5: 787-795.
19. Tomoyasu, T., A. Mogk, H. Langen, P. Goloubinoff, and B. Bukau. 2001. Genetic dissection of the roles of chaperones and proteases in protein folding and degradation in the *Escherichia coli* cytosol. Mol. Microbiol. 40: 397-413.
20. Voet, D., and J. G. Voet. 2004. Biochemistry. 3rd ed. John Wiley & Sons. NY.
21. White, D., R. J. Sharp, and F. G. Priest. 1993. A polyphasic taxonomic study of thermophilic bacilli from a wide geographical area. Antonie van Leeuwenhoek 64: 357-386.
22. Ziegler, K., S. M. Noble, E. Mutumanje, B. Bishop, D. P. Huddler, and T. L. Born. 2007. Identification of catalytic cysteine, histidine, and lysine residues in *Escherichia coli* homoserine transsuccinyllase. Biochemistry 46: 2674-2683.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for increasing or decreasing the thermostability or acid tolerance of a microbe, comprising the steps of: mutating a nucleotide sequence which encodes Homoserine o-succinyltransferase (Met A) consisting of the amino acid sequence of SEQ ID NO:41 to obtain a nucleic acid molecule encoding a mutant MetA; transforming a microbial host cell with the nucleic acid molecule encoding the mutant MetA; and culturing the microbial host cell transformed with the nucleic acid molecule encoding the mutant MetA to express the mutant MetA, thereby increasing or decreasing the thermostability or acid tolerance of the transformed microbial host cell, wherein the mutant MetA comprises the substitution mutation of: (a) Thr for Ser at position 61 of SEQ ID NO:41; (b) Val for Glu at position 213 of SEQ ID NO:41; (c) Thr for Ile at position 229 of SEQ ID NO:41; (d) Asp for Asn at position 267 of SEQ ID NO:41; (e) Lys for Asn at position 271 of SEQ ID NO:41; (g) Val for Leu at position 110 of SEQ ID NO:41; (h) Leu for Ile at position 124 of SEQ ID NO:41; (i) Leu for Arg at position 160 of SEQ ID NO:41; (j) Thr for Ala at position 195 of SEQ ID NO:41; (k) Glu for Ala at position 200 of SEQ ID NO:41; (l) Gly for Asp at position 218 of SEQ ID NO:41; (m) Tyr for Ile at position 229 of SEQ ID NO:41; or (n) Tyr for Phe at position 247 of SEQ ID NO:41.

2. The method of claim 1, wherein the mutant MetA induces the increase of the thermostability or acid tolerance of the microbe and comprises the substitution of: (a) Thr for Ser at position 61 of SEQ ID NO:41; (b) Val for Glu at position 213 of SEQ ID NO:41; (c) Thr for Ile at position 229 of SEQ ID NO:41; (d) Asp for Asn at position 267 of SEQ ID NO:41; (e) Lys for Asn at position 271 of SEQ ID NO:41; (g) Val for Leu at position 110 of SEQ ID NO:41; (h) Leu for Ile at position 124 of SEQ ID NO:41; (k) Glu for Ala at position 200 of SEQ ID NO:41; (m) Tyr for Ile at position 229 of SEQ ID NO:41; or (n) Tyr for Phe at position 247 of SEQ ID NO:41.

3. The method of claim 1, wherein the mutant MetA induces the decrease of the thermostability or acid tolerance of the microbe and comprises the substitution of: (i) Leu for Arg at position 160 of SEQ ID NO:41; (j) Thr for Ala at position 195 of SEQ ID NO:41; or (l) Gly for Asp at position 218 of SEQ ID NO:41.

4. A method for increasing or decreasing the thermostability or acid tolerance of homoserine o-succinyltransferase (MetA), comprising conferring a substitution mutation to MetA consisting of the amino acid sequence of SEQ ID NO:41 to prepare a mutant MetA, wherein the mutant MetA comprises the substitution mutation of: (a) Thr for Ser at position 61 of SEQ ID NO:41; (b) Val for Glu at position 213 of SEQ ID NO:41; (c) Thr for Ile at position 229 of SEQ ID NO:41; (d) Asp for Asn at position 267 of SEQ ID NO:41; (e) Lys for Asn at position 271 of SEQ ID NO:41; (g) Val for Leu at position 110 of SEQ ID NO:41; (h) Leu for Ile at position 124 of SEQ ID NO:41; (i) Leu for Arg at position 160 of SEQ ID NO:41; (j) Thr for Ala at position 195 of SEQ ID NO:41; (k) Glu for Ala at position 200 of SEQ ID NO:41; (l) Gly for Asp at position 218 of SEQ ID NO:41; (m) Tyr for Ile at position 229 of SEQ ID NO:41; or (n) Tyr for Phe at position 247 of SEQ ID NO:41.

5. The method of claim 4, wherein the substitution mutation induces the increase of the thermostability or acid tolerance of MetA and the mutant MetA comprises the substitution of: (a) Thr for Ser at position 61 of SEQ ID NO:41; (b) Val for Glu at position 213 of SEQ ID NO:41; (c) Thr for Ile at position 229 of SEQ ID NO:41; (d) Asp for Asn at position 267 of SEQ ID NO:41; (e) Lys for Asn at position 271 of SEQ ID NO:41; (g) Val for Leu at position 110 of SEQ ID NO:41; (h) Leu for Ile at position 124 of SEQ ID NO:41; (k) Glu for Ala at position 200 of SEQ ID NO:41; (m) Tyr for Ile at position 229 of SEQ ID NO:41; or (n) Tyr for Phe at position 247 of SEQ ID NO:41.

6. The method of claim 4, wherein the substitution mutation induces the decrease of the thermostability or acid tolerance of MetA and the mutant MetA comprises the substitution of: (i) Leu for Arg at position 160 of SEQ ID NO:41; (j) Thr for Ala at position 195 of SEQ ID NO:41; or (l) Gly for Asp at position 218 of SEQ ID NO:41.

7. The method of claim 1, wherein the mutant MetA comprises the substitution of: (c) Thr for Be at position 229 of SEQ ID NO:41; (d) Asp for Asn at position 267 of SEQ ID NO:41; (h) Leu for Ile at position 124 of SEQ ID NO:41; (i) Leu for Arg at position 160 of SEQ ID NO:41; or (m) Tyr for Ile at position 229 of SEQ ID NO:41.

8. The method of claim 1, wherein the microbe is a mesophilic bacterium.

9. The method of claim 8, wherein the mesophilic bacterium is a member of a genus selected from the group consisting of *Escherichia, Pseudomonas, Xanthomonas, Serratia, Lactobacillus, Bacillus, Citrobacter, Salmonella* and *Klebsiella*.

* * * * *

SEQUENCE LISTING

```
<160> NUMBER OF SEQ ID NOS: 69

<210> SEQ ID NO 1
<211> LENGTH: 930
<212> TYPE: DNA
<213> ORGANISM: Artificial Sequence
<220> FEATURE:
<223> OTHER INFORMATION: nucleotide sequence of mutant MetA

<400> SEQUENCE: 1
atgccgattc gtgtgccgga cgagctaccc gccgtcaatt tcttgcgtga agaaaacgtc      60
tttgtgatga caacttctcg tgcgtctggt caggaaattc gtccacttaa ggttctgatc     120
cttaacctga tgccgaagaa gattgaaact gaaaatcagt ttctgcgcct gctttcaaac     180
acacctttgc aggtcgatat tcagctgttg cgcatcgatt cccgtgaatc gcgcaacacg     240
cccgcagagc atctgaacaa cttctactgt aactttgaag atattcagga tcagaacttt     300
gacggtttga ttgtaactgg tgcgccgctg ggcctggtgg agtttaatga tgtcgcttac      360
```

```
tggccgcaga tcaaacaggt gctggagtgg tcgaaagatc acgtcacctc gacgctgttt    420
gtctgctggg cggtacaggc cgcgctcaat atcctctacg gcattcctaa gcaaactcgc    480
accgaaaaac tctctggcgt ttacgagcat catattctcc atcctcatgc gcttctgacg    540
cgtggctttg atgattcatt cctggcaccg cattcgcgct atgctgactt tccggcagcg    600
ttgattcgtg attacaccga tctggaaatt ctggcagtga cggaagaagg ggatgcatat    660
ctgtttgcca gtaaagataa gcgcactgcc tttgtgacgg ccatcccga atatgatgcg    720 caaacgctgg cgcaggaatt tttccgcgat gtggaagccg gactagaccc ggatgtaccg    780
tataactatt tcccgcacga tgatccgcaa aagacaccgc gagcgagctg gcgtagtcac    840
ggtaatttac tgtttaccaa ctggctcaac tattacgtct accagatcac gccatacgat    900
ctacggcaca tgaatccaac gctggattaa                                    930
```

<210> SEQ ID NO 2
<211> LENGTH: 309
<212> TYPE: PRT
<213> ORGANISM: Artificial Sequence
<220> FEATURE:
<223> OTHER INFORMATION: amino acid sequence of mutant MetA

<400> SEQUENCE: 2

```
Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Thr Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Val Thr Glu Glu Gly Asp Ala Tyr Leu Phe Ala Ser
    210                 215                 220

Lys Asp Lys Arg Thr Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asp Asp Pro Gln Lys Thr
```

```
              260                 265                 270
Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
        290                 295                 300

Asn Pro Thr Leu Asp
305

<210> SEQ ID NO 3
<211> LENGTH: 30
<212> TYPE: DNA
<213> ORGANISM: Artificial Sequence
<220> FEATURE:
<223> OTHER INFORMATION: metA1

<400> SEQUENCE: 3
cgcctactcg agatcgcaac gagttcctcc                                      30

<210> SEQ ID NO 4
<211> LENGTH: 40
<212> TYPE: DNA
<213> ORGANISM: Artificial Sequence
<220> FEATURE:
<223> OTHER INFORMATION: metA2

<400> SEQUENCE: 4
gcctcaaagc ttcatatgct gattacctca ctacatacgc                           40

<210> SEQ ID NO 5
<211> LENGTH: 27
<212> TYPE: DNA
<213> ORGANISM: Artificial Sequence
<220> FEATURE:
<223> OTHER INFORMATION: metA3

<400> SEQUENCE: 5
cgcctccata tgccgattcg tgtgccg                                         27

<210> SEQ ID NO 6
<211> LENGTH: 33
<212> TYPE: DNA
<213> ORGANISM: Artificial Sequence
<220> FEATURE:
<223> OTHER INFORMATION: metA4

<400> SEQUENCE: 6
cgcctcaagc ttggtgcctg aggtaaggtg ctg                                  33

<210> SEQ ID NO 7
<211> LENGTH: 22
<212> TYPE: DNA
<213> ORGANISM: Artificial Sequence
<220> FEATURE:
<223> OTHER INFORMATION: metA5

<400> SEQUENCE: 7
gtagtgaggt aatcagcata tg                                              22

<210> SEQ ID NO 8
<211> LENGTH: 37
<212> TYPE: DNA
<213> ORGANISM: Artificial Sequence
<220> FEATURE:
<223> OTHER INFORMATION: metA8
```

<400> SEQUENCE: 8
atctggatgt ctaaacgtat aagcgtatgt agtgagg                                    37

<210> SEQ ID NO 9
<211> LENGTH: 36
<212> TYPE: DNA
<213> ORGANISM: Artificial Sequence
<220> FEATURE:
<223> OTHER INFORMATION: metA9

<400> SEQUENCE: 9
atcgcttaac gatcgactat cacagaagat taatcc                                     36

<210> SEQ ID NO 10
<211> LENGTH: 31
<212> TYPE: DNA
<213> ORGANISM: Artificial Sequence
<220> FEATURE:
<223> OTHER INFORMATION: Geo1

<400> SEQUENCE: 10
cgcctccata tgccaatcaa cattccaaaa g                                          31

<210> SEQ ID NO 11
<211> LENGTH: 21
<212> TYPE: DNA
<213> ORGANISM: Artificial Sequence
<220> FEATURE:
<223> OTHER INFORMATION: Geo2

<400> SEQUENCE: 11
cagggcgatt gtcgaaacac g                                                     21

<210> SEQ ID NO 12
<211> LENGTH: 64
<212> TYPE: DNA
<213> ORGANISM: Artificial Sequence
<220> FEATURE:
<223> OTHER INFORMATION: Geo4

<400> SEQUENCE: 12
atctggatgt ctaaacgtat aagcgtatgt agtgaggtaa tcaggttatg ccaatcaaca          60
ttcc                                                                        64

<210> SEQ ID NO 13
<211> LENGTH: 71
<212> TYPE: DNA
<213> ORGANISM: Artificial Sequence
<220> FEATURE:
<223> OTHER INFORMATION: Geo5

<400> SEQUENCE: 13
atcgcttaac gatcgactat cacagaagat taatccagcg ttggattcat cagggcgatt          60
gtcgaaacac g                                                                71

<210> SEQ ID NO 14
<211> LENGTH: 32
<212> TYPE: DNA
<213> ORGANISM: Artificial Sequence
<220> FEATURE:
<223> OTHER INFORMATION: metT

<400> SEQUENCE: 14
gcctgctttc aaacacacac ctttgcaggt cg                                         32

<210> SEQ ID NO 15
<211> LENGTH: 33
<212> TYPE: DNA
<213> ORGANISM: Artificial Sequence
<220> FEATURE:
<223> OTHER INFORMATION: metT2

<400> SEQUENCE: 15
gccagtaaag ataagcgcac tgcctttgtg acg        33

<210> SEQ ID NO 16
<211> LENGTH: 33
<212> TYPE: DNA
<213> ORGANISM: Artificial Sequence
<220> FEATURE:
<223> OTHER INFORMATION: metD

<400> SEQUENCE: 16
ctatttcccg cacgatgatc cgcaaaatac acc        33

<210> SEQ ID NO 17
<211> LENGTH: 27
<212> TYPE: DNA
<213> ORGANISM: Artificial Sequence
<220> FEATURE:
<223> OTHER INFORMATION: metK

<400> SEQUENCE: 17
gatccgcaaa agacaccgcg agcgagc        27

<210> SEQ ID NO 18
<211> LENGTH: 30
<212> TYPE: DNA
<213> ORGANISM: Artificial Sequence
<220> FEATURE:
<223> OTHER INFORMATION: metV

<400> SEQUENCE: 18
ctggaaattc tggcagtgac ggaagaaggg        30

<210> SEQ ID NO 19
<211> LENGTH: 24
<212> TYPE: DNA
<213> ORGANISM: Artificial Sequence
<220> FEATURE:
<223> OTHER INFORMATION: K3-forward

<400> SEQUENCE: 19
aaggatcaga actttgacgg tttg        24

<210> SEQ ID NO 20
<211> LENGTH: 25
<212> TYPE: DNA
<213> ORGANISM: Artificial Sequence
<220> FEATURE:
<223> OTHER INFORMATION: K3-reverse

<400> SEQUENCE: 20
aatatcttca aagttacagt agaag        25

<210> SEQ ID NO 21
<211> LENGTH: 23
<212> TYPE: DNA
<213> ORGANISM: Artificial Sequence
<220> FEATURE:

<223> OTHER INFORMATION: V3-forward

<400> SEQUENCE: 21
ggtgggcctg gtggagttta atg                                        23

<210> SEQ ID NO 22
<211> LENGTH: 23
<212> TYPE: DNA
<213> ORGANISM: Artificial Sequence
<220> FEATURE:
<223> OTHER INFORMATION: V3-reverse

<400> SEQUENCE: 22
ggcgcaccag ttacaatcaa acc                                        23

<210> SEQ ID NO 23
<211> LENGTH: 23
<212> TYPE: DNA
<213> ORGANISM: Artificial Sequence
<220> FEATURE:
<223> OTHER INFORMATION: L2-forward

<400> SEQUENCE: 23
cagctcaaac aggtgctgga gtg                                        23

<210> SEQ ID NO 24
<211> LENGTH: 25
<212> TYPE: DNA
<213> ORGANISM: Artificial Sequence
<220> FEATURE:
<223> OTHER INFORMATION: L2-reverse

<400> SEQUENCE: 24
cggccagtaa gcgacatcat taaac                                      25

<210> SEQ ID NO 25
<211> LENGTH: 23
<212> TYPE: DNA
<213> ORGANISM: Artificial Sequence
<220> FEATURE:
<223> OTHER INFORMATION: L1-forward

<400> SEQUENCE: 25
ctctcaccga aaactctct ggc                                         23

<210> SEQ ID NO 26
<211> LENGTH: 23
<212> TYPE: DNA
<213> ORGANISM: Artificial Sequence
<220> FEATURE:
<223> OTHER INFORMATION: L1-reverse

<400> SEQUENCE: 26
tttgcttagg aatgccgtag agg                                        23

<210> SEQ ID NO 27
<211> LENGTH: 25
<212> TYPE: DNA
<213> ORGANISM: Artificial Sequence
<220> FEATURE:
<223> OTHER INFORMATION: T4-forward

<400> SEQUENCE: 27
ctatactgac tttccggcag cgttg                                      25

```
<210> SEQ ID NO 28
<211> LENGTH: 26
<212> TYPE: DNA
<213> ORGANISM: Artificial Sequence
<220> FEATURE:
<223> OTHER INFORMATION: T4-reverse

<400> SEQUENCE: 28
cgcgaatgcg gtgccaggaa tgaatc                                      26

<210> SEQ ID NO 29
<211> LENGTH: 24
<212> TYPE: DNA
<213> ORGANISM: Artificial Sequence
<220> FEATURE:
<223> OTHER INFORMATION: E1-forward

<400> SEQUENCE: 29
cagagttgat tcgtgattac accg                                        24

<210> SEQ ID NO 30
<211> LENGTH: 25
<212> TYPE: DNA
<213> ORGANISM: Artificial Sequence
<220> FEATURE:
<223> OTHER INFORMATION: E1-reverse

<400> SEQUENCE: 30
ccggaaagtc agcatagcgc gaatg                                       25

<210> SEQ ID NO 31
<211> LENGTH: 25
<212> TYPE: DNA
<213> ORGANISM: Artificial Sequence
<220> FEATURE:
<223> OTHER INFORMATION: G1-forward

<400> SEQUENCE: 31
ggtgcatatc tgtttgccag taaag                                       25

<210> SEQ ID NO 32
<211> LENGTH: 27
<212> TYPE: DNA
<213> ORGANISM: Artificial Sequence
<220> FEATURE:
<223> OTHER INFORMATION: G1-reverse

<400> SEQUENCE: 32
cccttcttcc gtctctgcca gaatttc                                     27

<210> SEQ ID NO 33
<211> LENGTH: 24
<212> TYPE: DNA
<213> ORGANISM: Artificial Sequence
<220> FEATURE:
<223> OTHER INFORMATION: Y2-forward

<400> SEQUENCE: 33
gaatatttcc gcgatgtgga agcc                                        24

<210> SEQ ID NO 34
<211> LENGTH: 27
<212> TYPE: DNA
<213> ORGANISM: Artificial Sequence
<220> FEATURE:
<223> OTHER INFORMATION: Y2-reverse
```

```
<400> SEQUENCE: 34
ctgcgccagc gtttgcgcat catattc                                              27

<210> SEQ ID NO 35
<211> LENGTH: 35
<212> TYPE: DNA
<213> ORGANISM: Artificial Sequence
<220> FEATURE:
<223> OTHER INFORMATION: MetY-forward

<400> SEQUENCE: 35
gccagtaaag ataagcgcta cgcctttgtg acggg                                     35

<210> SEQ ID NO 36
<211> LENGTH: 35
<212> TYPE: DNA
<213> ORGANISM: Artificial Sequence
<220> FEATURE:
<223> OTHER INFORMATION: MetY-reverse

<400> SEQUENCE: 36
cccgtcacaa aggcgtagcg cttatcttta ctggc                                     35

<210> SEQ ID NO 37
<211> LENGTH: 302
<212> TYPE: PRT
<213> ORGANISM: geobacillus

<400> SEQUENCE: 37
```

Met Pro Ile Asn Ile Pro Lys Asp Leu Pro Ala Lys Glu Ile Leu Glu
1               5                   10                  15

Gln Glu Asn Ile Phe Val Met Asp Glu Glu Arg Ala Tyr Ser Gln Asp
            20                  25                  30

Ile Arg Pro Leu Asn Ile Ile Ile Leu Asn Leu Met Pro Glu Lys Glu
        35                  40                  45

Lys Ala Glu Thr Gln Leu Leu Arg Leu Leu Gly Asn Ser Pro Leu Gln
    50                  55                  60

Val Asn Val Thr Phe Leu Arg Pro Ala Thr His Glu Pro Lys Thr Thr
65                  70                  75                  80

Ser Lys His His Leu Glu Gln Phe Tyr Thr Ile Phe Pro His Ile Arg
                85                  90                  95

His Arg Lys Phe Asp Gly Met Ile Ile Thr Gly Ala Pro Val Glu Gln
            100                 105                 110

Met Pro Phe Glu Glu Val Asn Tyr Trp Gly Glu Leu Thr Glu Ile Met
        115                 120                 125

Glu Trp Thr Lys Thr Asn Val Thr Ser Thr Leu His Ile Cys Trp Gly
    130                 135                 140

Ala Gln Ala Gly Leu Tyr Tyr His Tyr Gly Ile Pro Lys Tyr Pro Leu
145                 150                 155                 160

Pro Glu Lys Cys Phe Gly Val Phe Asn His Thr Val Glu Val Lys Asn
                165                 170                 175

Val Lys Leu Leu Arg Gly Phe Asp Asp Val Phe Arg Met Pro His Ser
            180                 185                 190

Arg His Thr Asp Val Lys Arg Glu Asp Ile Glu Lys Val Pro Asp Leu
        195                 200                 205

Thr Ile Leu Ser Met Ser Asp Lys Ala Gly Val Cys Leu Val Ala Ser
    210                 215                 220

Asn Asp Gly Arg Arg Ile Phe Leu Thr Gly His Pro Glu Tyr Asp Ala

```
225                 230                 235                 240

Thr Thr Leu Lys Glu Glu Tyr Glu Arg Asp Leu Ala Lys Gly Leu Pro
                245                 250                 255

Ile His Ile Pro Glu Ser Tyr Phe Pro Asn Asp Gln Pro Ser Gln Pro
            260                 265                 270

Pro Leu Asn Thr Trp Arg Ser His Ala Asn Leu Leu Phe Val Asn Trp
        275                 280                 285

Leu Asn Tyr Tyr Val Tyr Gln Glu Thr Pro Tyr Glu Trp Glu
    290                 295                 300

<210> SEQ ID NO 38
<211> LENGTH: 305
<212> TYPE: PRT
<213> ORGANISM: clostridium

<400> SEQUENCE: 38

Met Pro Ile Lys Ile Pro Asp Ser Leu Pro Ala Lys Glu Val Leu Thr
1               5                   10                  15

Asn Glu Asn Ile Phe Val Met Asp Glu His Arg Ala Leu His Gln Asp
            20                  25                  30

Val Arg Pro Leu Arg Ile Ala Ile Leu Asn Leu Met Pro Thr Lys Ile
        35                  40                  45

Thr Thr Glu Thr Gln Leu Leu Arg Leu Ile Gly Asn Thr Pro Ile Gln
    50                  55                  60

Val Glu Ile Glu Leu Leu His Pro Lys Thr His Val Ser Lys Asn Thr
65                  70                  75                  80

Pro Glu Glu His Leu Thr Lys Phe Tyr Lys Thr Phe Asp Glu Val Lys
                85                  90                  95

Asp Glu Lys Phe Asp Gly Leu Ile Ile Thr Gly Ala Pro Val Glu Gln
            100                 105                 110

Met Glu Phe Glu Glu Val Asn Tyr Trp Glu Glu Leu Lys Lys Ile Met
        115                 120                 125

Asp Trp Ser Val His Asn Val Tyr Ser Thr Phe His Ile Cys Trp Gly
    130                 135                 140

Ala Gln Ala Ala Leu Tyr His His Tyr Gly Ile Lys Lys Tyr Pro Leu
145                 150                 155                 160

Lys Glu Lys Met Phe Gly Ile Phe Pro His Arg Ile Cys Lys Pro Asn
                165                 170                 175

Thr Met Leu Met Arg Gly Phe Asp Asp Cys Phe Tyr Ala Pro His Ser
            180                 185                 190

Arg His Thr Glu Val Arg Arg Glu Asp Ile Glu Lys Val Gly Glu Ile
        195                 200                 205

Asp Ile Leu Ser Asp Ser Glu Glu Ala Gly Val Tyr Ile Met Lys Thr
    210                 215                 220

Arg Gly Gly Arg Gln Val Phe Val Thr Gly His Ser Glu Tyr Asp Gln
225                 230                 235                 240

Phe Thr Leu Lys Glu Glu Tyr Glu Arg Asp Leu Ala Lys Gly Leu Lys
                245                 250                 255

Ile Lys Met Pro Lys Asn Tyr Phe Pro Asp Asp Asp Pro Thr Lys Pro
            260                 265                 270

Pro Val Val Asn Trp Arg Gly His Ala Asn Leu Leu Phe Ser Asn Trp
        275                 280                 285

Leu Asn Tyr Tyr Val Tyr Gln Glu Thr Pro Phe Asp Leu Asn Glu Leu
    290                 295                 300
```

Lys
305

<210> SEQ ID NO 39
<211> LENGTH: 304
<212> TYPE: PRT
<213> ORGANISM: thermotoga

<400> SEQUENCE: 39

```
Met Pro Ile Asn Val Pro Ser Gly Leu Pro Ala Val Lys Val Leu Ala
1               5                   10                  15

Lys Glu Gly Ile Phe Val Met Thr Glu Lys Arg Ala Ile His Gln Asp
            20                  25                  30

Ile Arg Pro Leu Glu Ile Leu Ile Leu Asn Leu Met Pro Asp Lys Ile
        35                  40                  45

Lys Thr Glu Ile Gln Leu Leu Arg Leu Leu Gly Asn Thr Pro Leu Gln
    50                  55                  60

Val Asn Val Thr Leu Leu Tyr Thr Glu Thr His Lys Pro Lys His Thr
65                  70                  75                  80

Pro Ile Glu His Ile Leu Lys Phe Tyr Thr Thr Phe Ser Ala Val Lys
                85                  90                  95

Asp Arg Lys Phe Asp Gly Phe Ile Ile Thr Gly Ala Pro Val Glu Leu
            100                 105                 110

Leu Pro Phe Glu Glu Val Asp Tyr Trp Glu Glu Leu Thr Glu Ile Met
        115                 120                 125

Glu Trp Ser Arg His Asn Val Tyr Ser Thr Met Phe Ile Cys Trp Ala
    130                 135                 140

Ala Gln Ala Gly Leu Tyr Tyr Phe Tyr Gly Ile Pro Lys Tyr Glu Leu
145                 150                 155                 160

Pro Gln Lys Leu Ser Gly Val Tyr Lys His Arg Val Ala Lys Asp Ser
                165                 170                 175

Val Leu Phe Arg Gly His Asp Asp Phe Phe Trp Ala Pro His Ser Arg
            180                 185                 190

Tyr Thr Glu Val Lys Lys Glu Asp Ile Asp Lys Val Pro Glu Leu Glu
        195                 200                 205

Ile Leu Ala Glu Ser Asp Glu Ala Gly Val Tyr Val Ala Asn Lys
    210                 215                 220

Ser Glu Arg Gln Ile Phe Val Thr Gly His Pro Glu Tyr Asp Arg Tyr
225                 230                 235                 240

Thr Leu Arg Asp Glu Tyr Tyr Arg Asp Ile Gly Arg Asn Leu Lys Val
                245                 250                 255

Pro Ile Pro Ala Asn Tyr Phe Pro Asn Asp Pro Thr Lys Thr Pro
            260                 265                 270

Ile Leu Thr Trp Trp Ser His Ala His Leu Phe Phe Ser Asn Trp Leu
        275                 280                 285

Asn Tyr Cys Ile Tyr Gln Lys Thr Pro Tyr Arg Leu Glu Asp Ile His
    290                 295                 300
```

<210> SEQ ID NO 40
<211> LENGTH: 314
<212> TYPE: PRT
<213> ORGANISM: streptococcus

<400> SEQUENCE: 40

```
Met Pro Ile Lys Leu Asp Asn Lys Leu Pro Ala Leu Asp Val Leu Arg
1               5                   10                  15
```

```
Ser Glu Asn Val Phe Ile Met Asp Glu Asn Arg Ala Ser Ser Gln Asp
             20                  25                  30

Ile Arg Pro Met Glu Val Leu Ile Leu Asn Leu Met Pro Thr Lys Glu
         35                  40                  45

Val Thr Glu Thr Gln Leu Leu Arg Leu Ala Asn Thr Pro Leu Gln
 50                  55                  60

Ile Asn Val Glu Phe Leu Tyr Met Ala Ser His Lys Ser Lys Asn Thr
 65                  70                  75                  80

His Ala Glu His Met Glu Thr Phe Tyr Lys Thr Phe Asp Glu Ile Lys
                 85                  90                  95

Asp Lys Tyr Tyr Asp Gly Leu Ile Val Thr Gly Ala Pro Val Glu Gln
            100                 105                 110

Met Pro Phe Glu Glu Val Asp Tyr Trp Gln Glu Leu Thr Arg Val Phe
        115                 120                 125

Asp Trp Ser Lys Lys His Val Tyr Ser Thr Leu His Leu Cys Trp Gly
    130                 135                 140

Ala Gln Ala Gly Leu Tyr Tyr Lys His Gly Val Asp Lys Phe Pro Leu
145                 150                 155                 160

Ser Glu Lys Leu Ser Gly Ile Tyr Lys Gln Thr Val Asp Met Pro Glu
                165                 170                 175

Asn Phe Leu Met Asn Gly Phe Asp Asp Ser Phe Val Ser Pro His Ser
            180                 185                 190

Arg Tyr Thr Glu Val Thr Leu Glu Asp Ile Lys Asn Lys Thr Asp Leu
        195                 200                 205

Asp Val Val Ala Ser Gly Gln Glu Val Gly Leu Ser Ile Leu Ala Ser
    210                 215                 220

Lys Asp Leu Arg Glu Val Tyr Ser Phe Gly His Phe Glu Tyr Asp Arg
225                 230                 235                 240

Asp Thr Leu Ala Arg Glu Tyr Arg Arg Asp Leu Glu Val Gly Ile Asn
                245                 250                 255

Pro Asp Val Pro Ala Asn Tyr Phe Pro Gly Asp Pro Ser Gln Glu
            260                 265                 270

Pro Lys Leu Arg Trp Asn Leu Ala Ala Ser Thr Phe Phe Ser Asn Trp
        275                 280                 285

Ile Asn Tyr Ala Val Tyr Gln Glu Thr Pro Tyr Arg Leu Glu Glu Leu
    290                 295                 300

Glu Asp Asp Phe Ser Phe Tyr Gly Tyr Leu
305                 310

<210> SEQ ID NO 41
<211> LENGTH: 309
<212> TYPE: PRT
<213> ORGANISM: Escherichia coli

<400> SEQUENCE: 41

Met Pro Ile Arg Val Pro Asp Glu Leu Pro Ala Val Asn Phe Leu Arg
 1               5                  10                  15

Glu Glu Asn Val Phe Val Met Thr Thr Ser Arg Ala Ser Gly Gln Glu
             20                  25                  30

Ile Arg Pro Leu Lys Val Leu Ile Leu Asn Leu Met Pro Lys Lys Ile
         35                  40                  45

Glu Thr Glu Asn Gln Phe Leu Arg Leu Leu Ser Asn Ser Pro Leu Gln
 50                  55                  60

Val Asp Ile Gln Leu Leu Arg Ile Asp Ser Arg Glu Ser Arg Asn Thr
 65                  70                  75                  80
```

```
Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Phe Arg Asp Val Glu Ala Gly Leu Asp
            245                 250                 255

Pro Asp Val Pro Tyr Asn Tyr Phe Pro His Asn Asp Pro Gln Asn Thr
        260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
290                 295                 300

Asn Pro Thr Leu Asp
305

<210> SEQ ID NO 42
<211> LENGTH: 355
<212> TYPE: PRT
<213> ORGANISM: methylococcus

<400> SEQUENCE: 42

Met Pro Leu Val Ala His Thr Asp Leu Pro Thr Phe Gln Arg Leu Arg
1               5                   10                  15

Glu Glu Gly Gln Asp Val Leu Ser Val Glu Arg Ala Ala Arg Gln Asp
            20                  25                  30

Ile Arg Glu Met His Ile Gly Leu Leu Asn Met Met Pro Asp Ala Ala
        35                  40                  45

Leu Glu Ala Thr Glu Arg Gln Phe Phe Arg Leu Val Gly Gly Ala Asn
50                  55                  60

Pro Ile Val Gln Phe His Met His Pro Phe Thr Ile Glu Gly Leu Pro
65                  70                  75                  80

Arg Gly Asp Gln Ala Ala Glu His Ile Ala Arg Tyr Tyr Glu Ser Phe
                85                  90                  95

Asp Arg Ile Arg Glu Glu Gly Leu Asp Gly Leu Ile Val Ser Gly Ala
            100                 105                 110

Asn Val Thr Gln Pro His Leu Gln Gln Glu Ala Phe Trp Gln Pro Leu
        115                 120                 125

Thr Glu Val Phe Asp Trp Ala Arg Ser Asn Val Thr Ser Ile Leu Cys
```

-continued

```
            130                 135                 140
Ser Cys Leu Ala Thr His Ala Leu Phe Gln Tyr Ser Tyr Gly Val Glu
145                 150                 155                 160

Arg Thr His Leu Gly Phe Lys Arg Trp Gly Val Tyr Ser His Arg Val
                165                 170                 175

Val Glu Pro Leu His Pro Leu Val Ala Asp Ile Asn Thr Arg Phe Asp
            180                 185                 190

Val Pro His Ser Arg Tyr Asn Glu Ile Phe Arg Glu Asp Met Glu Ala
        195                 200                 205

Ala Gly Leu Arg Val Leu Val Glu Ser Glu Glu Ala Gly Val His Leu
    210                 215                 220

Ala Val Ser Pro Asp Leu Phe Arg Val Ile Tyr Phe Gln Ala His Pro
225                 230                 235                 240

Glu Tyr Asp Thr Val Ser Leu Leu Lys Glu Tyr Lys Arg Glu Ile Leu
                245                 250                 255

Arg Tyr Phe Ser Gly Glu Arg Glu Asp Tyr Pro Pro Phe Pro Glu His
            260                 265                 270

Tyr Phe Ser Leu Glu Val Gly Ala Ala Leu Asn Asp Tyr Gly Gln Ala
        275                 280                 285

Leu Arg Ser Ala Arg Arg Ala Gly Arg Ala Pro Pro Pro Phe Pro Asp
    290                 295                 300

Glu Phe Val Leu Arg His Leu Asp Asn Thr Trp Arg Asp Thr Ala Lys
305                 310                 315                 320

Ala Val Phe Asn Asn Trp Leu Gly Lys Ile Tyr Gln Ile Thr Asp Gln
                325                 330                 335

Asp Arg Arg Lys Pro Phe Met Ala Ile Ile Asp Pro Asp Asn Pro Leu
            340                 345                 350

Gly Leu Ala
        355

<210> SEQ ID NO 43
<211> LENGTH: 309
<212> TYPE: PRT
<213> ORGANISM: Shigella

<400> SEQUENCE: 43

Met Pro Ile Arg Val Leu Asp Glu Leu Pro Ala Val Asn Phe Leu Arg
1               5                   10                  15

Glu Glu Asn Val Phe Val Met Thr Thr Ser Arg Ala Ser Gly Gln Glu
                20                  25                  30

Ile Arg Pro Leu Lys Val Leu Ile Leu Asn Leu Met Pro Lys Lys Ile
            35                  40                  45

Glu Thr Glu Asn Gln Phe Leu Arg Leu Ser Asn Ser Pro Leu Gln
        50                  55                  60

Ile Asp Ile Gln Leu Leu Arg Ile Asp Ala Arg Glu Ser Arg Asn Ile
65                  70                  75                  80

Pro Ala Glu His Leu Asn Asn Phe Tyr Cys Asn Phe Glu Asp Ile Cys
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ala Lys Asp His Val Thr Ser Thr Leu Phe Val Cys Trp Ala
    130                 135                 140
```

```
Val Gln Ala Ala Leu Asn Ile Leu Tyr Gly Ile Pro Lys Gln Thr Arg
145                 150                 155                 160

Thr Asp Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

His Thr Leu Ala Ser Glu Tyr Phe Arg Asp Val Glu Ala Gly Leu Ser
                245                 250                 255

Pro Asn Val Pro Tyr Asn Tyr Phe Pro Lys Asn Asp Pro Gln Asn Lys
            260                 265                 270

Pro Arg Ala Thr Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
290                 295                 300

Asn Pro Thr Leu Asp
305

<210> SEQ ID NO 44
<211> LENGTH: 309
<212> TYPE: PRT
<213> ORGANISM: Salmonella

<400> SEQUENCE: 44

Met Pro Ile Arg Val Leu Asp Glu Leu Pro Ala Val Asn Phe Leu Arg
1               5                   10                  15

Glu Glu Asn Val Phe Val Met Thr Thr Ser Arg Ala Ser Gly Gln Glu
                20                  25                  30

Ile Arg Pro Leu Lys Val Leu Ile Leu Asn Leu Met Pro Lys Lys Ile
            35                  40                  45

Glu Thr Glu Asn Gln Phe Leu Arg Leu Ser Asn Ser Pro Leu Gln
50                  55                  60

Val Asp Ile Gln Leu Leu Arg Ile Asp Ala Arg Glu Ser Arg Asn Ile
65                  70                  75                  80

Pro Ala Glu His Leu Asn Asn Phe Tyr Cys Asn Phe Asp Asp Ile Cys
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Arg Gln Val Leu
        115                 120                 125

Glu Trp Ala Lys Asp His Val Thr Ser Thr Leu Phe Val Cys Trp Ala
130                 135                 140

Val Gln Ala Ala Leu Asn Ile Leu Tyr Gly Ile Pro Lys Gln Thr Arg
145                 150                 155                 160

Thr Asp Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205
```

```
Glu Ile Leu Ala Glu Thr Glu Gly Asp Ala Tyr Leu Phe Ala Ser
        210                 215                 220

Lys Asp Lys Arg Ile Ala Phe Val Thr Gly His Pro Glu Tyr Asp Ala
225                 230                 235                 240

His Thr Leu Ala Gly Glu Tyr Phe Arg Asp Val Glu Ala Gly Leu Asn
                245                 250                 255

Pro Glu Val Pro Tyr Asn Tyr Phe Pro Lys Asn Asp Pro Gln Asn Ile
            260                 265                 270

Pro Arg Ala Thr Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
    290                 295                 300

Asn Pro Thr Leu Asp
305

<210> SEQ ID NO 45
<211> LENGTH: 309
<212> TYPE: PRT
<213> ORGANISM: Klebsiella

<400> SEQUENCE: 45

Met Pro Ile Arg Val Gln Asp Glu Leu Pro Ala Val Asn Phe Leu Arg
1               5                   10                  15

Asn Glu Asn Val Phe Val Met Thr Thr Thr Arg Ala Thr Thr Gln Glu
                20                  25                  30

Ile Arg Pro Leu Lys Val Leu Ile Leu Asn Leu Met Pro Lys Lys Ile
            35                  40                  45

Glu Thr Glu Asn Gln Phe Leu Arg Leu Leu Ser Asn Ser Pro Leu Gln
        50                  55                  60

Val Asp Ile Gln Leu Leu Arg Ile Asp Ala Arg Glu Ser Arg Asn Ile
65                  70                  75                  80

Pro Ala Glu His Leu Asn Asn Phe Tyr Cys Asn Phe Asp Glu Ile Cys
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ala Lys Asp His Val Thr Ser Thr Leu Phe Val Cys Trp Ala
130                 135                 140

Val Gln Ala Ala Leu Asn Ile Leu Tyr Gly Ile Pro Lys Gln Thr Arg
145                 150                 155                 160

Ala Glu Lys Thr Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Gly Leu Ile Arg Asp Tyr Thr Asp Leu
        195                 200                 205

Glu Ile Leu Ala Glu Thr Glu Glu Gly Asp Ala Tyr Leu Phe Ala Ser
        210                 215                 220

Lys Asp Lys Arg Ile Ala Phe Val Thr Gly His Pro Glu Tyr Asp Ala
225                 230                 235                 240

Asn Thr Leu Ala Ser Glu Tyr Phe Arg Asp Val Glu Ala Gly Leu Asn
                245                 250                 255

Pro Glu Ile Pro His Asn Tyr Phe Pro Gln Asn Asp Pro Gln Asn Lys
```

260                 265                 270
Pro Arg Ala Thr Trp Arg Ser His Gly Asn Leu Leu Phe Ala Asn Trp
            275                 280                 285

Leu Asn Tyr Tyr Val Tyr Gln Ile Thr Pro Tyr Asp Leu Arg His Met
        290                 295                 300

Asn Pro Thr Leu Asp
305

<210> SEQ ID NO 46
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 46

Leu Ser Asn Ser Pro Leu Gln Val
1               5

<210> SEQ ID NO 47
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 47

Ile Leu Ala Glu Thr Glu Asp Gly
1               5

<210> SEQ ID NO 48
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 48

Ile Leu Ala Glu Thr Glu Glu Gly
1               5

<210> SEQ ID NO 49
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 49

Asp Lys Arg Ile Ala Phe Val Thr
1               5

<210> SEQ ID NO 50
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 50

Tyr Phe Pro Lys Asn Asp Pro Gln
1               5

<210> SEQ ID NO 51
<211> LENGTH: 8

```
<212> TYPE: PRT
<213> ORGANISM: Artificial Sequence
<220> FEATURE:
<223> OTHER INFORMATION: partial amino acid sequence of MetA

<400> SEQUENCE: 51

Tyr Phe Pro His Asn Asp Pro Gln
1               5

<210> SEQ ID NO 52
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 52

Tyr Phe Pro Gln Asn Asp Pro Gln
1               5

<210> SEQ ID NO 53
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 53

Asp Pro Gln Asn Lys Pro Arg Ala
1               5

<210> SEQ ID NO 54
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 54

Asp Pro Gln Asn Ile Pro Arg Ala
1               5

<210> SEQ ID NO 55
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 55

Asp Pro Gln Asn Thr Pro Arg Ala
1               5

<210> SEQ ID NO 56
<211> LENGTH: 8
<212> TYPE: PRT
<213> ORGANISM: Artificial Sequence
<220> FEATURE:
<223> OTHER INFORMATION: partial amino acid sequence of MetA
<220> FEATURE:
<221> NAME/KEY: PEPTIDE
<222> LOCATION: (1)..(8)
<223> OTHER INFORMATION: first and second Xaa independently represent
      Glu or Asp

<400> SEQUENCE: 56

Xaa Xaa Ile Gln Asp Gln Asn Phe
1               5
```

```
<210> SEQ ID NO 57
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 57

Gly Ala Pro Leu Gly Leu Val Glu
1               5

<210> SEQ ID NO 58
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 58

Trp Pro Gln Ile Lys Gln Val Leu
1               5

<210> SEQ ID NO 59
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 59

Trp Pro Gln Ile Arg Gln Val Leu
1               5

<210> SEQ ID NO 60
<211> LENGTH: 8
<212> TYPE: PRT
<213> ORGANISM: Artificial Sequence
<220> FEATURE:
<223> OTHER INFORMATION: partial amino acid sequence of MetA
<220> FEATURE:
<221> NAME/KEY: PEPTIDE
<222> LOCATION: (1)..(8)
<223> OTHER INFORMATION: first Xaa is Ile, Thr or Ala; second Xaa is Asp
      or Glu; third Xaa is Leu or Ile

<400> SEQUENCE: 60

Lys Gln Thr Arg Xaa Xaa Lys Xaa
1               5

<210> SEQ ID NO 61
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 61

Ser Arg Tyr Ala Asp Phe Pro Arg
1               5

<210> SEQ ID NO 62
<211> LENGTH: 8
<212> TYPE: PRT
<213> ORGANISM: Artificial Sequence
<220> FEATURE:
<223> OTHER INFORMATION: partial amino acid sequence of MetA
```

```
<400> SEQUENCE: 62

Ser Arg Tyr Ala Asp Phe Pro Gly
1               5

<210> SEQ ID NO 63
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 63

Phe Pro Ala Ala Leu Ile Arg Asp
1               5

<210> SEQ ID NO 64
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 64

Glu Asp Gly Asp Ala Tyr Leu Phe
1               5

<210> SEQ ID NO 65
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 65

Glu Glu Gly Asp Ala Tyr Leu Phe
1               5

<210> SEQ ID NO 66
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 66

Asp Lys Arg Ile Ala Phe Val Thr
1               5

<210> SEQ ID NO 67
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 67

Ala Ser Glu Phe Phe Arg Asp Val
1               5

<210> SEQ ID NO 68
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 68
```

```
Ala Gln Glu Phe Phe Arg Asp Val
1               5

<210> SEQ ID NO 69
<211> LENGTH: 8
<212> TYPE: PRT
<213> ORGANISM: Artificial Sequence
<220> FEATURE:
<223> OTHER INFORMATION: partial amino acid sequence of MetA

<400> SEQUENCE: 69

Ala Gly Glu Phe Phe Arg Asp Val
1               5
```